(12) United States Patent
Stokes et al.

(10) Patent No.: US 7,094,201 B1
(45) Date of Patent: Aug. 22, 2006

(54) SYSTEM AND METHOD FOR GENETICALLY TREATING CARDIAC CONDUCTION DISTURBANCES

(75) Inventors: Kenneth B. Stokes, Anoka, MN (US); Josée Morissette, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/376,317

(22) Filed: Aug. 18, 1999

Related U.S. Application Data

(63) Continuation of application No. 08/682,277, filed on Jul. 17, 1996, now abandoned.

(51) Int. Cl.
*A61N 1/05* (2006.01)
*A61N 1/36* (2006.01)
*A61K 48/00* (2006.01)
*C12N 15/36* (2006.01)

(52) U.S. Cl. ............. 600/120; 600/119; 600/122; 600/9; 514/44; 435/320.1

(58) Field of Classification Search ............. 435/69.1, 435/320.1; 514/44; 604/24, 28, 93, 96; 607/9, 119, 120, 122
See application file for complete search history.

(56) References Cited

U.S. PATENT DOCUMENTS

| | | | | |
|---|---|---|---|---|
| 4,360,031 A | 11/1982 | White | | 128/786 |
| 4,699,147 A | 10/1987 | Chilson | | 128/642 |
| 4,711,251 A | 12/1987 | Stokes | | 128/784 |
| 5,019,034 A | * 5/1991 | Weaver et al. | | 604/20 |
| 5,030,204 A | 7/1991 | Badger | | 604/95 |
| 5,041,107 A | 8/1991 | Heil | | 604/891.1 |
| 5,060,660 A | 10/1991 | Gambale | | 128/772 |
| 5,176,641 A | 1/1993 | Idriss | | 604/133 |
| 5,297,549 A | 3/1994 | Beatty | | 128/642 |
| 5,397,339 A | 3/1995 | Desai | | 607/116 |
| 5,443,450 A | 8/1995 | Kratoska | | 604/141 |
| 5,797,870 A | 8/1998 | March | | 604/49 |
| 6,567,705 B1 | 5/2003 | Stokes et al. | | 607/120 |
| 6,665,563 B1 | 12/2003 | Stokes et al. | | 607/3 |

FOREIGN PATENT DOCUMENTS

| | | |
|---|---|---|
| WO | WO 93/04724 | 3/1993 |
| WO | WO 94/11506 | 5/1994 |
| WO | WO 94/11506 | * 3/1995 |
| WO | WO 95/05781 | * 3/1995 |

OTHER PUBLICATIONS

Kanter et al, J. Mol. Cell. Cardiol. 26: 861-868, 1994.*
E. Marshall, Gene therapy growing pains; 1995 Science, vol. 269:1050-1055.*
Orkin et. al., Report and recommendations of the panel to assess the NIH investment in research on gene therapy, 1995.*
Alexander, M.Y. et al, Clin Exp Pharmacol Physiol 1999, Sep. 26 (9) 661-668.
Maurice, J.P., et al, J. Clin. Invest. Jul. 1999; 104(1) pp. 21-29.
Ascadi, et al., *The New Biol.*, 1991, 3, 71-81.
Barr, et al., *Gene Ther.*, 1994, 1, 51-58.
Chomczynsky, et al., *Anal. Biochem.*, 1987, 162, 156-159.
Davis, et al., *J. Am. Coll. Cardiol.*, 1994, 24, 1124-1132.
Fishman, et al., *J. Cell Biol.*, 1990, 111, 589-598.
French, et al., *Circulation*, 1994, 90, 2414-2424.
Gal, et al., *Lab. Invest.*, 1993, 68, 18-25.
Gluzman, et al., in *Eukaryotic Viral Vectors*, Gluzman, ed., Cold Spring Harbor Press, 1982, pp. 187-192.
Gourdie, et al., *J. Cell Sci.*, 1993, 105, 985-991.
Kanter, et al., *J. Mol. Cell Cardiol.*, 1994, 26, 861-868.
Kriegler, M. "Gene Transfer and Expression, a Laboratory Manual", W.H. Freeman Co., New York (1990).
Murry, E.J. e.d. "Methods in Molecular Biology", vol. 7, Humana Press, Inc., Cliffton, New Jersey (1991).
Parmacek, et al., *J. Biol. Chem.*, 1990, 265, 15970-15976.
Parmacek, et al., *Mol. Cell Biol.*, 1992, 12, 1967-1976.
Saffitz, et al., *J. Card. Electrophys.*, 1995, 6, 498-510.
Sambrook et al., *Molecular Cloning: A Laboratory Manual*, Second Ed. Cold Spring Harbor Press (1989), pp. 7.26-7.29.
Sambrook et al., *Molecular Cloning: A Laboratory Manual*, Second Ed. Cold Spring Harbor Press (1989), pp. 16.1-16.55.

* cited by examiner

*Primary Examiner*—Anne M. Wehbe'
(74) *Attorney, Agent, or Firm*—Ken Collier; Thomas F. Woods; Michael Jaro

(57) ABSTRACT

The present invention provides delivery systems for and methods of delivering conduction protein genetic material to cardiac cells in localized areas of the heart to improve the conductance therein. More specifically, there is provided a system and method for delivering connexin proteins or nucleic acid molecules encoding connexin proteins to a site in the heart which has been determined by mapping procedures to have a conduction disturbance. For cases where conduction is impaired, selected genetic material is delivered to cells around the disturbance area, in order to enhance overall conductivity patterns; in other cases, genetic material is selected to slow conduction in affected areas, so as to prevent, e.g., brady-tachy syndrome.

1 Claim, 6 Drawing Sheets

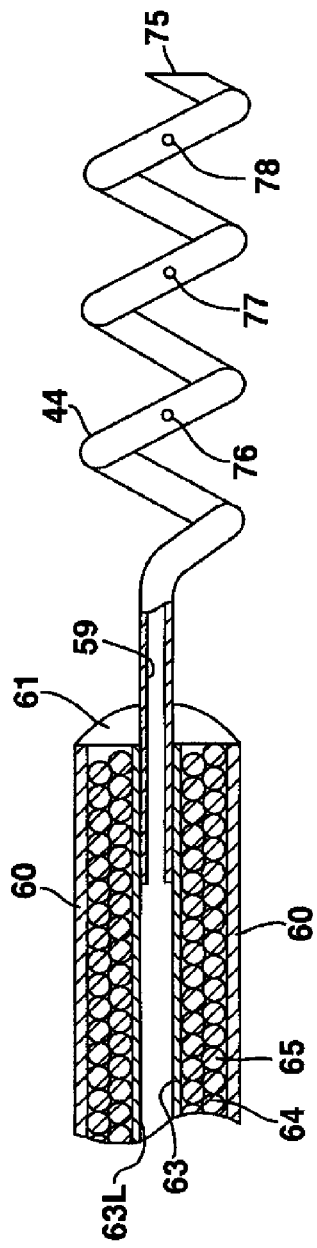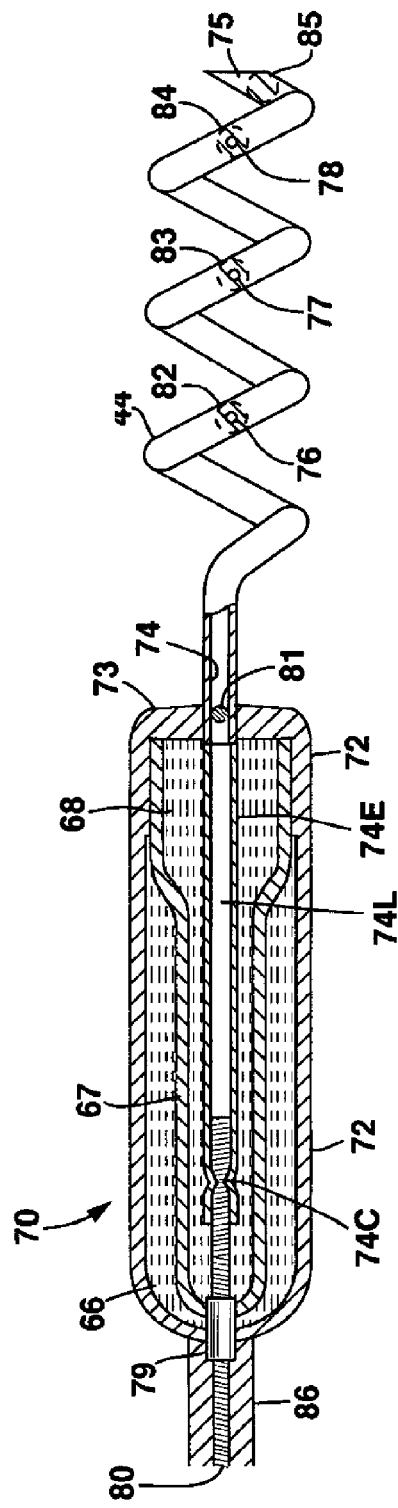

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 1074 bases
      (B) TYPE: nucleic acid
      (C) STRANDEDNESS: double
      (D) TOPOLOGY: linear (xi) SEQUENCE DESCRIPTION: SEQ ID NO:1:

```
ATG GGC GAT TGG AGC TTC CTG GGA AAT TTC CTG GAG GAA GTA CAC          45
Met Gly Asp Trp Ser Phe Leu Gly Asn Phe Leu Glu Glu Val His
 1               5                  10                  15

AAG CAC TCG ACC GTG GTA GGC AAG GTC TGG CTC ACT GTC CTC TTC          90
Lys His Ser Thr Val Val Gly Lys Val Trp Leu Thr Val Leu Phe
                20                  25                  30

ATA TTC CGT ATG CTC GTG CTG GGC ACA GCT GCT GAG TCT ACC TGG         135
Ile Phe Arg Met Leu Val Leu Gly Thr Ala Ala Glu Ser Thr Trp
                35                  40                  45

GGG GAT GAG CAG GCT GAT TTC CGG TGT GAT ACG ATT CAG CCT GGC         180
Gly Asp Glu Gln Ala Asp Phe Arg Cys Asp Thr Ile Gln Pro Gly
                50                  55                  60

TGC CAC AAT GTC TGC TAC GAC CAG GCT TTC CCC ATC TCC CAC ATT         225
Cys His Asn Val Cys Tyr Asp Gln Ala Phe Pro Ala Ser His Ile
                65                  70                  75

CGC TAC TGG GTG CTG CAG ATC ATC TTC GTC TCT ACG CCC TCT CTG         270
Arg Tyr Trp Val Leu Gln Ile Ile Phe Val Ser Thr Pro Ser Leu
                80                  85                  90

GTG TAC ATG GGC CAC GCC ATG CAC ACT GTG CGC ATG CAG GAG AAG         315
Val Tyr Met Gly His Ala Met His Thr Val Arg Met Gln Glu Lys
                95                  100                 105

CGC AAG CTA CGG GAG GCC GAG AGG GCC AAA GAG GTC CGG GGC TCT         360
Arg Lys Leu Arg Glu Ala Glu Arg Ala Lys Glu Val Arg Gly Ser
                110                 115                 120

GGC TCT TAC GAG TAC CCG GTG GCA GAG AAG GCA GAA CTG TCC TGC         405
```

-continued

```
                Gly Ser Tyr Glu Tyr Pro Val Ala Glu Lys Ala Glu Leu Ser Cys
                            125                 130                 135

TGG GAG GAA GGG AAT GGA AGG ATT GCC CTC CAG GGC ACT CTG CTC           450
Trp Glu Glu Gly Asn Gly Arg Ile Ala Leu Gln Gly Thr Leu Leu
                140                 145                 150

AAC ACC TAT GTG TGC AGC ATC CTG ATC CGC ACC ACC ATG GAG GTG           495
Asn Thr Tyr Val Cys Ser Ile Leu Ile Arg Thr Thr Met Glu Val
                155                 160                 165

GGC TTC ATT GTG GGC CAG TAC TTC ATC TAC GGA ATC TTC CTG ACC           540
Gly Phe Ile Val Gly Gln Tyr Phe Ile Tyr Gly Ile Phe Leu Thr
                170                 175                 180

ACC CTG CAT GTC TGC CGC AGG AGT CCC TGT CCC CAC CCG GTC AAC           585
Thr Leu His Val Cys Arg Arg Ser Pro Cys Pro His Pro Val Asn
                185                 190                 195

TGT TAC GTA TCC CGG CCC ACA GAG AAG AAT GTC TTC ATT GTC TTT           630
Cys Tyr Val Ser Arg Pro Thr Glu Lys Asn Val Phe Ile Val Phe
                200                 205                 210

ATG CTG GCT GTG GCT GCA CTG TCC CTC CTC CTT AGC CTG GCT GAA           675
Met Leu Ala Val Ala Ala Leu Ser Leu Leu Leu Ser Leu Ala Glu
                215                 220                 225

CTC TAC CAC CTG GGC TGG AAG AAG ATC AGA CAG CGA TTT GTC AAA           720
Leu Tyr His Leu Gly Trp Lys Lys Ile Arg Gln Arg Phe Val Lys
                230                 235                 240

CCG CGG CAG TAC ATG GCT AAG TGC CAG CTT TCT GGC CCT CTG TGG           765
Pro Arg Gln Tyr Met Ala Lys Cys Gln Leu Ser Gly Pro Leu Trp
                245                 250                 255

GCT ATA GTC CAG AGC TGC ACA CCA CCC CCC GAC TTT AAT CAG TGC           810
Ala Ile Val Gln Ser Cys Thr Pro Pro Pro Asp Phe Asn Gln Cys
                260                 265                 270

CTG GAG AAT GGT CCT GGG GGA AAA TTC TTC AAT CCC TTC AGC AAT           855
Leu Glu Asn Gly Pro Gly Gly Lys Phe Phe Asn Pro Phe Ser Asn
                275                 280                 285

AAT ATG GCC TCC CAA CAA AAC ACA GAC AAC CTG GTC ACC GAG CAA           900
Asn Met Ala Ser Gln Gln Asn Thr Asp Asn Leu Val Thr Glu Gln
                290                 295                 300

GTA CGA GGT CAG GAG CAG ACT CCT GGG GAA GGT TTC ATC CAG GTT           945
Val Arg Gly Gln Glu Gln Thr Pro Gly Glu Gly Phe Ile Gln Val
                305                 310                 315

CGT TAT GGC CAG AAG CCT GAG GTG CCC AAT GGA GTC TCA CCA GGT           990
Arg Tyr Gly Gln Lys Pro Glu Val Pro Asn Gly Val Ser Pro Gly
                320                 325                 330

CAC CGC CTT CCC CAT GGC TAT CAT AGT GAC AAG CGA CGT CTT AGT          1035
His Arg Leu Pro His Gly Tyr His Ser Asp Lys Arg Arg Leu Ser
                335                 340                 345

AAG GCC AGC AGC AAG GCA AGG TCA GAT GAC CTA TCA GTG               1074
Lys Ala Ser Ser Lys Ala Arg Ser Asp Asp Leu Ser Val
                350                 355
```

(2) INFORMATION FOR SEQ ID NO:2:

(i) SEQUENCE CHARACTERISTICS:
        (A) LENGTH: 358 amino acids
        (B) TYPE: amino acid
        (C) STRANDEDNESS: single
        (D) TOPOLOGY: unknown (xi) SEQUENCE DESCRIPTION: SEQ ID NO:2:

```
Met Gly Asp Trp Ser Phe Leu Gly Asn Phe Leu Glu Glu Val His
 1               5                  10                  15

Lys His Ser Thr Val Val Gly Lys Val Trp Leu Thr Val Leu Phe
                20                  25                  30
```

```
Ile Phe Arg Met Leu Val Leu Gly Thr Ala Ala Glu Ser Thr Trp
                 35                  40                  45

Gly Asp Glu Gln Ala Asp Phe Arg Cys Asp Thr Ile Gln Pro Gly
                 50                  55                  60

Cys His Asn Val Cys Tyr Asp Gln Ala Phe Pro Ala Ser His Ile
                 65                  70                  75

Arg Tyr Trp Val Leu Gln Ile Ile Phe Val Ser Thr Pro Ser Leu
                 80                  85                  90

Val Tyr Met Gly His Ala Met His Thr Val Arg Met Gln Glu Lys
                 95                 100                 105

Arg Lys Leu Arg Glu Ala Glu Arg Ala Lys Glu Val Arg Gly Ser
                110                 115                 120

Gly Ser Tyr Glu Tyr Pro Val Ala Glu Lys Ala Glu Leu Ser Cys
                125                 130                 135

Trp Glu Glu Glu Asn Gly Arg Ile Ala Leu Gln Gly Thr Leu Leu
                140                 145                 150

Asn Thr Tyr Val Cys Ser Ile Leu Ile Arg Thr Thr Met Glu Val
                155                 160                 165

Gly Phe Ile Val Gly Gln Tyr Phe Ile Tyr Gly Ile Phe Leu Thr
                170                 175                 180

Thr Leu His Val Cys Arg Arg Ser Pro Cys Pro His Pro Val Asn
                185                 190                 195

Cys Tyr Val Ser Arg Pro Thr Glu Lys Asn Val Phe Ile Val Phe
                200                 205                 210

Met Leu Ala Val Ala Ala Leu Ser Leu Leu Ser Leu Ala Glu
                215                 220                 225

Leu Tyr His Leu Gly Trp Lys Lys Ile Arg Gln Arg Phe Val Lys
                230                 235                 240

Pro Arg Gln Trp Met Ala Lys Cys Gln Leu Ser Gly Pro Leu Trp
                245                 250                 255

Ala Ile Val Gln Ser Cys Thr Pro Pro Asp Phe Asn Gln Cys
                260                 265                 270

Leu Glu Asn Gly Pro Gly Gly Lys Phe Phe Asn Pro Phe Ser Asn
                275                 280                 285

Asn Met Ala Ser Gln Gln Asn Thr Asp Asn Leu Val Thr Glu Gln
                290                 295                 300

Val Arg Gly Gln Glu Gln Thr Pro Gly Glu Gly Phe Ile Gln Val
                305                 310                 315

Arg Tyr Gly Gln Lys Pro Glu Val Pro Asn Gly Val Ser Pro Gly
                320                 325                 330

His Arg Leu Pro His Gly Tyr His Ser Asp Lys Arg Arg Leu Ser
                335                 340                 345

Lys Ala Ser Ser Lys Ala Arg Ser Asp Asp Leu Ser Val
                350                 355

(2) INFORMATION FOR SEQ ID NO:3:

(i) SEQUENCE CHARACTERISTICS:
            (A) LENGTH: 1146 bases
            (B) TYPE: nucleic acid
            (C) STRANDEDNESS: double
            (D) TOPOLOGY: linear (xi) SEQUENCE DESCRIPTION: SEQ ID NO:3:

ATG GGT GAC TGG AGC GCC TTA GGC AAA CTC CTT GAC AAG GTT CAA                    45
```

```
                                                -continued

Met Gly Asp Trp Ser Ala Leu Gly Lys Leu Leu Asp Lys Val Gln
 1               5                  10                  15

GCC TAC TCA ACT GCT GGA GGG AAG GTG TGG CTG TCA GTA CTT TTC         90
Ala Tyr Ser Thr Ala Gly Gly Lys Val Trp Leu Ser Val Leu Phe
                 20                  25                  30

ATT TTC CGA ATC CTG CTG CTG GGG ACA GCG GTT GAG TCA GCC TGG        135
Ile Phe Arg Ile Leu Leu Leu Gly Thr Ala Val Glu Ser Ala Trp
                 35                  40                  45

GGA GAT GAG CAG TCT GCC TTT CGT TGT AAC ACT CAG CAA CCT GGT        180
Gly Asp Glu Gln Ser Ala Phe Arg Cys Asn Thr Gln Gln Pro Gly
                 50                  55                  60

TGT GAA AAT GTC TGC TAT GAC AAG TCT TTC CCA ATC TCT CAT GTG        225
Cys Glu Asn Val Cys Tyr Asp Lys Ser Phe Pro Ile Ser His Val
                 65                  70                  75

CGC TTC TGG GTC CTG CAG ATC ATA TTT GTG TCT GTA CCC ACA CTC        270
Arg Phe Trp Val Leu Gln Ile Ile Phe Val Ser Val Pro Thr Leu
                 80                  85                  90

TTG TAC CTG GCT CAT GTG TTC TAT GTG ATG CGA AAG GAA GAG AAA        315
Leu Tyr Leu Ala His Val Phe Tyr Val Met Arg Lys Glu Glu Lys
                 95                 100                 105

CTG AAC AAG AAA GAG GAA GAA CTC AAG GTT GCC CAA ACT GAT GGT        360
Leu Asn Lys Lys Glu Glu Glu Leu Lys Val Ala Gln Thr Asp Gly
                110                 115                 120

GTC AAT GTG GAC ATG CAC TTG AAG CAG ATT GAG ATA AAG AAG TTC        405
Val Asn Val Asp Met His Leu Lys Gln Ile Glu Ile Lys Lys Phe
                125                 130                 135

AAG TAC GGT ATT GAA GAG CAT GGT AAG GTG AAA ATG CGA GGG GGG        450
Lys Tyr Gly Ile Glu Glu His Gly Lys Val Lys Met Arg Gly Gly
                140                 145                 150

TTG CTG CGA ACC TAC ATC ATC AGT ATC CTC TTC AAG TCT ATC TTT        495
Leu Leu Arg Thr Tyr Ile Ile Ser Ile Leu Phe Lys Ser Ile Phe
                155                 160                 165

GAG GTG GCC TTC TTG CTG ATC CAG TGG TAC ATC TAT GGA TTC AGC        540
Glu Val Ala Phe Leu Leu Ile Gln Trp Tyr Ile Tyr Gly Phe Ser
                170                 175                 180

TTG AGT GCT GTT TAC ACT TGC AAA AGA GAT CCC TGC CCA CAT CAG        585
Leu Ser Ala Val Tyr Thr Cys Lys Arg Asp Pro Cys Pro His Gln
                185                 190                 195

GTG GAC TGT TTC CTC TCT CGC CCC ACG GAG AAA ACC ATC TTC ATC        630
Val Asp Cys Phe Leu Ser Arg Pro Thr Glu Lys Thr Ile Phe Ile
                200                 205                 210

ATC TTC ATG CTG GTG GTG TCC TTG GTG TCC CTG GCC TTG AAT ATC        675
Ile Phe Met Leu Val Val Ser Leu Val Ser Leu Ala Leu Asn Ile
                215                 220                 225

ATT GAA CTC TTC TAT GTT TTC TTC AAG GGC GTT AAG GAT CGG GTT        720
Ile Glu Leu Phe Tyr Val Phe Phe Lys Gly Val Lys Asp Arg Val
                230                 235                 240

AAG GGA AAG AGC GAC CCT TAC CAT GCG ACC AGT GGT GCG CTG AGC        765
Lys Gly Lys Ser Asp Pro Tyr His Ala Thr Ser Gly Ala Leu Ser
                245                 250                 255

CCT GCC AAA GAC TGT GGG TCT CAA AAA TAT GCT TAT TTC AAT GGC        810
Pro Ala Lys Asp Cys Gly Ser Gln Lys Tyr Ala Try Phe Asn Gly
                260                 265                 270

TGC TCC TCA CCA ACC GCT CCC CTC TCG CCT ATG TCT CCT CCT GGG        855
Cys Ser Ser Pro Thr Ala Pro Leu Ser Pro Met Ser Pro Pro Gly
                275                 280                 285

TAC AAG CTG GTT ACT GGC GAC AGA AAC AAT TCT TCT TGC CGC AAT        900
Tyr Lys Leu Val Thr Gly Asp Arg Asn Asn Ser Ser Cys Arg Asn
                290                 295                 300
```

```
TAC AAC AAG CAA GCA AGT GAG CAA AAC TGG GCT AAT TAC AGT GCA        945
Tyr Asn Lys Gln Ala Ser Glu Gln Asn Trp Ala Asn Tyr Ser Ala
                305                 310                 315

GAA CAA AAT CGA ATG GGG CAG GCG GGA AGC ACC ATC TCT AAC TCC        990
Glu Gln Asn Arg Met Gly Gln Ala Gly Ser Thr Ile Ser Asn Ser
            320                 325                 330

CAT GCA CAG CCT TTT GAT TTC CCC GAT GAT AAC CAG AAT TCT AAA       1035
His Ala Gln Pro Phe Asp Phe Pro Asp Asp Asn Gln Asn Ser Lys
            335                 340                 345

AAA CTA GCT GCT GGA CAT GAA TTA CAG CCA CTA GCC ATT GTG GAC       1080
Lys Leu Ala Ala Gly His Glu Leu Gln Pro Lei Ala Ile Val Asp
                350                 355                 360

CAG CGA CCT TCA AGC AGA GCC AGC AGT CGT GCC AGC AGC AGA CCT       1125
Gln Arg Pro Ser Ser Arg Ala Ser Ser Arg Ala Ser Ser Arg Pro
            365                 370                 375

CGG CCT GAT GAC CTG GAG ATC                                       1146
Arg Pro Asp Asp Leu Glu Ile
            380
```

(2) INFORMATION FOR SEQ ID NO:4:

(i) SEQUENCE CHARACTERISTICS:
        (A) LENGTH: 382 amino acids
        (B) TYPE: amino acid
        (C) STRANDEDNESS: single
        (D) TOPOLOGY: unknown (xi) SEQUENCE DESCRIPTION: SEQ ID NO:4:

```
Met Gly Asp Trp Ser Ala Leu Gly Lys Leu Leu Asp Lys Val Gln
  1               5                  10                  15

Ala Tyr Ser Thr Ala Gly Gly Lys Val Trp Leu Ser Val Leu Phe
                 20                  25                  30

Ile Phe Arg Ile Leu Leu Leu Gly Thr Ala Val Glu Ser Ala Trp
                 35                  40                  45

Gly Asp Glu Gln Ser Ala Phe Arg Cys Asn Thr Gln Gln Pro Gly
                 50                  55                  60

Cys Glu Asn Val Cys Tyr Asp Lys Ser Phe Pro Ile Ser His Val
                 65                  70                  75

Arg Phe Trp Val Leu Gln Ile Ile Phe Val Ser Val Pro Thr Leu
                 80                  85                  90

Leu Tyr Leu Ala His Val Phe Tyr Val Met Arg Lys Glu Glu Lys
                 95                 100                 105

Leu Asn Lys Lys Glu Glu Glu Leu Lys Val Ala Gln Thr Asp Gly
                110                 115                 120

Val Asn Val Asp Met His Leu Lys Gln Ile Glu Ile Lys Lys Phe
                125                 130                 135

Lys Tyr Gly Ile Glu Glu His Gly Lys Val Lys Met Arg Gly Gly
                140                 145                 150

Leu Leu Arg Thr Tyr Ile Ile Ser Ile Leu Phe Lys Ser Ile Phe
                155                 160                 165

Glu Val Ala Phe Leu Leu Ile Gln Trp Tyr Ile Tyr Gly Phe Ser
                170                 175                 180

Leu Ser Ala Val Tyr Thr Cys Lys Arg Asp Pro Cys Pro His Gln
                185                 190                 195

Val Asp Cys Phe Leu Ser Arg Pro Thr Glu Lys Thr Ile Phe Ile
                200                 205                 210

Ile Phe Met Leu Val Val Ser Leu Val Ser Leu Ala Leu Asn Ile
                215                 220                 225
```

```
Ile Glu Leu Phe Tyr Val Phe Lys Gly Val Lys Asp Arg Val
            230             235             240

Lys Gly Lys Cys Asp Pro Tyr His Ala Thr Ser Gly Ala Leu Ser
            245             250             255

Pro Ala Lys Asp Cys Gly Ser Gln Lys Tyr Ala Tyr Phe Asn Gly
            260             265             270

Cys Ser Ser Pro Thr Ala Pro Leu Ser Pro Met Ser Pro Pro Gly
            275             280             285

Tyr Lys Leu Val Thr Gly Asp Arg Asn Asn Ser Ser Cys Arg Asn
            290             295             300

Tyr Asn Lys Gln Ala Ser Glu Gln Asn Trp Ala Asn Tyr Ser Ala
            305             310             315

Glu Gln Asn Arg Met Gly Gly Ala Gly Ser Thr Ile Ser Asn Ser
            320             325             330

His Ala Gln Pro Phe Asp Phe Pro Asp Asn Gln Asn Ser Lys
            335             340             345

Lys Leu Ala Ala Gly His Glu Leu Gln Pro Leu Ala Ile Val Asp
            350             355             360

Gln Arg Pro Ser Ser Arg Ala Ser Ser Arg Ala Ser Ser Arg Pro
            365             370             375

Arg Pro Asp Asp Leu Glu Ile
            380
```

(2) INFORMATION FOR SEQ ID NO:5:

(i) SEQUENCE CHARACTERISTICS:
        (A) LENGTH: 1188 bases
        (B) TYPE: nucleic acid
        (C) STRANDEDNESS: double
        (D) TOPOLOGY: linear (xi) SEQUENCE DESCRIPTION: SEQ ID NO:5:

```
ATG AGT TGG AGC TTT CTG ACT CGC CTG CTA GAG GAG ATT CAC AAC                45
Met Ser Trp Ser Phe Leu Thr Arg Leu Leu Glu Glu Ile His Asn
 1               5                  10                  15

CAT TCC ACA TTT GTG GGG AAG ATC TGG CTC ACT GTT CTG ATT GTC                90
His Ser Thr Phe Val Gly Lys Ile Trp Leu Thr Val Leu Ile Val
                20                  25                  30

TTC CGG ATC GTC CTT ACA GCT GTA GGA GGA GAA TCC ATC TAT TAC               135
Phe Arg Ile Val Leu Thr Ala Val Gly Gly Glu Ser Ile Tyr Tyr
                35                  40                  45

GAT GAG CAA AGC AAA TTT GTG TGC AAC ACA GAA CAG CCG GGC TGT               180
Asp Glu Gln Ser Lys Phe Val Cys Asn Thr Glu Gln Pro Gly Cys
                50                  55                  60

GAG AAT GTC TGT TAT GAT GCG TTT GCA CCT CTC TCC CAT GTA CGC               225
Glu Asn Val Cys Tyr Asp Ala Phe Ala Pro Leu Ser His Val Arg
                65                  70                  75

TTC TGG GTG TTC CAG ATC ATC CTG GTG GCA ACT CCC TCT GTG ATG               270
Phe Trp Val Phe Gln Ile Ile Leu Val Ala Thr Pro Ser Val Met
                80                  85                  90

TAC CTG GGC TAT GCT ATC CAC AAG ATT GCC AAA ATG GAG CAC GGT               315
Tyr Leu Gly Tyr Ala Ile His Lys Ile Ala Lys Met Glu His Gly
                95                 100                 105

GAA GCA GAC AAG AAG GCA GCT CGG AGC AAG CCC TAT GCA ATG CGC               360
Glu Ala Asp Lys Lys Ala Ala Arg Ser Lys Pro Tyr Ala Met Arg
               110                 115                 120

TGG AAA CAA CAC CGG GCT CTG GAA GAA ACG GAG GAG GAC AAC GAA               405
Trp Lys Gln His Arg Ala Leu Glu Glu Thr Glu Glu Asp Asn Glu
```

```
                    125                 130                 135
GAG GAT CCT ATG ATG TAT CCA GAG ATG GAG TTA GAA AGT GAT AAG           450
Glu Asp Pro Met Met Tyr Pro Glu Met Glu Leu Glu Ser Asp Lys
                    140                 145                 150

GAA AAT AAA GAG CAG AGC CAA CCC AAA CCT AAG CAT GAT GGC CGA           495
Glu Asn Lys Glu Gln Ser Gln Pro Lys Pro Lys His Asp Gly Arg
                    155                 160                 165

CGA CGG ATT CGG GAA GAT GGG CTC ATG AAA ATC TAT GTG CTG CAG           540
Arg Arg Ile Arg Glu Asp Gly Leu Met Lys Ile Tyr Val Leu Gln
                    170                 175                 180

TTG CTG GCA AGG ACC GTG TTT GAG GTG GGT TTT CTG ATA GGG CAG           585
Leu Leu Ala Arg Thr Val Phe Glu Val Gly Phe Leu Ile Gly Gln
                    185                 190                 195

TAT TTT CTG TAT GGC TTC CAA GTC CAC CCG TTT TAT GTG TGC AGC           630
Tyr Phe Leu Tyr Gly Phe Gln Val His Pro Phe Tyr Val Cys Ser
                    200                 205                 210

AGA CTT CCT TGT CCT CAT AAG ATA GAC TGC TTT ATT TCT AGA CCC           675
Arg Leu Pro Cys Pro His Lys Ile Asp Cys Phe Ile Ser Arg Pro
                    215                 220                 225

ACT GAA AAG ACC ATC TTC CTT CTG ATA ATG TAT GGT GTT ACA GGC           720
Thr Glu Lys Thr Ile Phe Leu Leu Ile Met Tyr Gly Val Thr Gly
                    230                 235                 240

CTT TGC CTC TTG CTT AAC ATT TGG GAG ATG CTT CAT TTA GGG TTT           765
Leu Cys Leu Leu Leu Asn Ile Trp Glu Met Leu His Leu Gly Phe
                    245                 250                 255

GGG ACC ATT CGA GAC TCA CTA AAC AGT AAA AGG AGG GAA CTT GAG           810
Gly Thr Ile Arg Asp Ser Leu Asn Ser Lys Arg Arg Glu Leu Glu
                    260                 265                 270

GAT CCG GGT GCT TAT AAT TAT CCT TTC ACT TGG AAT ACA CCA TCT           855
Asp Pro Gly Ala Tyr Asn Tyr Pro Phe Thr Trp Asn Thr Pro Ser
                    275                 280                 285

GCT CCC CCT GGC TAT AAC ATT GCT GTC AAA CCA GAT CAA ATC CAG           900
Ala Pro Pro Gly Tyr Asn Ile Ala Val Lys Pro Asp Gln Ile Gln
                    290                 295                 300

TAC ACC GAA CTG TCC AAT GCT AAG ATC GCC TAC AAG CAA AAC AAG           945
Tyr Thr Glu Leu Ser Asn Ala Lys Ile Ala Tyr Lys Gln Asn Lys
                    305                 310                 315

GCC AAC ACA GCC CAG GAA CAG CAG TAT GGC AGC CAT GAG GAG AAC           990
Ala Asn Thr Ala Gln Glu Gln Gln Tyr Gly Ser His Glu Glu Asn
                    320                 325                 330

CTC CCA GCT GAC CTG GAG GCT CTG CAG CGG GAG ATC AGG ATG GCT          1035
Leu Pro Ala Asp Leu Glu Ala Leu Gln Arg Glu Ile Arg Met Ala
                    335                 340                 345

CAG GAA CGC TTG GAT CTG GCA GTT CAG GCC TAC AGT CAC CAA AAC          1080
Gln Glu Arg Leu Asp Leu Ala Val Gln Ala Tyr Ser His Gln Asn
                    350                 355                 360

AAC CCT CAT GGT CCC CGG GAG AAG AAG GCC AAA GTG GGG TCC AAA          1125
Asn Pro His Gly Pro Arg Glu Lys Lys Ala Lys Val Gly Ser Lys
                    365                 370                 375

GCT GGG TCC AAC AAA AGC ACT GCC AGT AGC AAA TCA GGG GAT GGG          1170
Ala Gly Ser Asn Lys Ser Thr Ala Ser Ser Lys Ser Gly Asp Gly
                    380                 385                 390

AAG AAC TCT GTC TGG ATT                                              1188
Lys Asn Ser Val Trp Ile
                    395

(2) INFORMATION FOR SEQ ID NO:6:

(i) SEQUENCE CHARACTERISTICS:
        (A) LENGTH: 396 amino acids
```

(B) TYPE: amino acid
        (C) STRANDEDNESS: single
        (D) TOPOLOGY: unknown (xi) SEQUENCE DESCRIPTION: SEQ ID NO:6:

Met Ser Trp Ser Phe Leu Thr Arg Leu Leu Glu Glu Ile His Asn
 1               5                  10                  15

His Ser Thr Phe Val Gly Lys Ile Trp Leu Thr Val Leu Ile Val
                20                  25                  30

Phe Arg Ile Val Leu Thr Ala Val Gly Gly Glu Ser Ile Tyr Tyr
                35                  40                  45

Asp Glu Gln Ser Lys Phe Val Cys Asn Thr Glu Gln Pro Gly Cys
                50                  55                  60

Glu Asn Val Cys Tyr Asp Ala Phe Ala Pro Leu Ser His Val Arg
                65                  70                  75

Phe Trp Val Phe Gln Ile Ile Leu Val Ala Thr Pro Ser Val Met
                80                  85                  90

Tyr Leu Gly Tyr Ala Ile His Lys Ile Ala Lys Met Glu His Gly
                95                  100                 105

Glu Ala Asp Lys Lys Ala Ala Arg Ser Lys Pro Tyr Ala Met Arg
                110                 115                 120

Trp Lys Gln His Arg Ala Leu Glu Glu Thr Glu Glu Asp Asn Glu
                125                 130                 135

Glu Asp Pro Met Met Tyr Pro Glu Met Glu Leu Glu Ser Asp Lys
                140                 145                 150

Glu Asn Lys Glu Gln Ser Gln Pro Lys Pro Lys His Asp Gly Arg
                155                 160                 165

Arg Arg Ile Arg Glu Asp Gly Leu Met Lys Ile Tyr Val Leu Gln
                170                 175                 180

Leu Leu Ala Arg Thr Val Phe Glu Val Gly Phe Leu Ile Gly Gln
                185                 190                 195

Tyr Phe Leu Tyr Gly Phe Gln Val His Pro Phe Tyr Val Cys Ser
                200                 205                 210

Arg Leu Pro Cys Pro His Lys Ile Asp Cys Phe Ile Ser Arg Pro
                215                 220                 225

Thr Glu Lys Thr Ile Phe Leu Leu Ile Met Tyr Gly Val Thr Gly
                230                 235                 240

Leu Cys Leu Leu Leu Asn Ile Trp Glu Met Leu His Leu Gly Phe
                245                 250                 255

Gly Thr Ile Arg Asp Ser Leu Asn Ser Lys Arg Arg Glu Leu Glu
                260                 265                 270

Asp Pro Gly Ala Tyr Asn Tyr Pro Phe Thr Trp Asn Thr Pro Ser
                275                 280                 285

Ala Pro Pro Gly Tyr Asn Ile Ala Val Lys Pro Asp Gln Ile Gln
                290                 295                 300

Tyr Thr Glu Leu Ser Asn Ala Lys Ile Ala Tyr Lys Gln Asn Lys
                305                 310                 315

Ala Asn Thr Ala Gln Glu Gln Gln Tyr Gly Ser His Glu Glu Asn
                320                 325                 330

Leu Pro Ala Asp Leu Glu Ala Leu Gln Arg Glu Ile Arg Met Ala
                335                 340                 345

Gln Glu Arg Leu Asp Leu Ala Val Gln Ala Tyr Ser His Gln Asn
                350                 355                 360

Asn Pro His Gly Pro Arg Glu Lys Lys Ala Lys Val Gly Ser Lys 365                 370                 375
Ala Gly Ser Asn Lys Ser Thr Ala Ser Ser Lys Ser Gly Asp Gly
                380                 385                 390
Lys Asn Ser Val Trp Ile
            395

(2) INFORMATION FOR SEQ ID NO:7:

(i) SEQUENCE CHARACTERISTICS:
        (A) LENGTH: 24 bases
        (B) TYPE: nucleic acid
        (C) STRANDEDNESS: single
        (D) TOPOLOGY: linear (xi) SEQUENCE DESCRIPTION: SEQ ID NO:7:

ATGCCTGACT GGACCGCCTT AGGC                                              24

(2) INFORMATION FOR SEQ ID NO:8:

(i) SEQUENCE CHARACTERISTICS:
        (A) LENGTH: 24 bases
        (B) TYPE: nucleic acid
        (C) STRANDEDNESS: single
        (D) TOPOLOGY: linear (xi) SEQUENCE DESCRIPTION: SEQ ID NO:8:

GATCTCGAGG TCATCAGGCC GAGG                                              24

(2) INFORMATION FOR SEQ ID NO:9:

(i) SEQUENCE CHARACTERISTICS:
        (A) LENGTH: 24 bases
        (B) TYPE: nucleic acid
        (C) STRANDEDNESS: single
        (D) TOPOLOGY: linear (xi) SEQUENCE DESCRIPTION: SEQ ID NO:9:

ATGAGTTGGA GCTTTCTGAC TCGC                                              24

(2) INFORMATION FOR SEQ ID NO:10:

(i) SEQUENCE CHARACTERISTICS:
        (A) LENGTH: 24 bases
        (B) TYPE: nucleic acid
        (C) STRANDEDNESS: single
        (D) TOPOLOGY: linear (xi) SEQUENCE DESCRIPTION: SEQ ID NO:10:

AATCCAGACA GAGTTCTTCC CATC                                              24

(2) INFORMATION FOR SEQ ID NO:11:

(i) SEQUENCE CHARACTERISTICS:
        (A) LENGTH: 24 bases
        (B) TYPE: nucleic acid
        (C) STRANDEDNESS: single
        (D) TOPOLOGY: linear (xi) SEQUENCE DESCRIPTION: SEQ ID NO:11:

ATGGGCGATT GGAGCTTCCT GGGA                                              24

(2) INFORMATION FOR SEQ ID NO:12:

(i) SEQUENCE CHARACTERISTICS:
        (A) LENGTH: 24 bases
        (B) TYPE: nucleic acid

```
        (C) STRANDEDNESS: single
        (D) TOPOLOGY: linear (xi) SEQUENCE DESCRIPTION: SEQ ID NO:12:

CACTGATAGG TCATCTGACC TTGC                                            24
```

SYSTEM AND METHOD FOR GENETICALLY TREATING CARDIAC CONDUCTION DISTURBANCES

This application is a continuation of application Ser. No. 08/682,277, filed Jul. 17, 1996 now abandoned.

FIELD OF THE INVENTION

The present invention relates to systems for and methods of delivering conduction protein genetic material to cardiac cells in localized areas of the heart to improve the conductance therein.

BACKGROUND OF THE INVENTION

The conduction system of the human heart is normally automatic, resulting in the contraction of the atria and ventricles by means of electrical impulses that originate in cardiac tissue. The cardiac cycle is separated into the contraction phase (systole) and relaxation phase (diastole). Although the rhythm of the cardiac cycle is intrinsic, the rate of this rhythm is modified by autonomic nerves and hormones such as epinephrine. The autonomic nervous system is comprised of parasympathetic and sympathetic nerves which release neurotransmitters such as acetylcholine and norepinephrine, respectively.

The natural pacemaker of the human heart is located in the posterior wall of the right atrium in a small area, approximately 2 by 5 by 15 mm, referred to as the sinoatrial node (SA node). The SA node initiates the cardiac cycle of systole and diastole phases by generating an electrical impulse that spreads over the right and left atria, causing them to contract almost simultaneously. This electrical impulse, referred to as the pacemaker potential, is created by the depolarization of the myocardial cells of the SA node, which results from changes in membrane permeability to cations. When the cell membrane is depolarized to about −30 mV, an action potential is produced. This impulse then passes to the atrioventricular node (AV node), which is located on the inferior portion of the interatrial septum. The impulse then continues through the atrioventricular bundle, referred to as the bundle of His, which is located at the top of the interventricular septum. The bundle of His divides into right and left branches which lead to the right and left ventricles respectively. Continuous with both branches of the bundle of His are the Purkinje fibers, which terminate within the ventricular walls. Stimulation of these fibers causes the ventricles to contract almost simultaneously and discharge blood into the pulmonary and systemic circulatory systems.

Abnormal patterns of electrical conduction in the heart can produce abnormalities of the cardiac cycle and seriously compromise the function of the heart, sometimes being fatal. For example, patients having such cardiac conduction disturbances may suffer from sick sinus syndrome (SSS), "brady-tachy syndrome," bradycardia, tachycardia, and heart block. Artificial pacemakers are often used in patients which suffer from these cardiac conduction disturbances.

In SSS, the conduction problem relates to, inter alia, intermittent reentry of the electrical impulse within the nodal tissue, sometimes resulting in rapid heart beats. A dual chamber pacemaker is often used to sense atrial activity and control the ventricle at the appropriate rate.

In some congenital diseases such as "brady-tachy syndrome," bradycardia, a slow rate of impulse, and tachycardia, a rapid rate of impulse, occur intermittently. The disease can be fatal where long pauses allow premature ventricular contractions (PVCs) to occur in multiples, initiating tachycardia. A pacemaker and/or cardioverter can be used to control episodes of tachycardia, and conventional demand type pacemakers have long been effective in treating bradycardia.

Excessive delay or failure of impulse transmission in abnormally slow impulse conduction is known as heart block. Heart block is often caused by scar tissue disrupting the conduction system. The cardiac impulse is believed to normally spread from the SA node along internodal pathways to the AV node and ventricles within 0.20 seconds. Heart block occurs in three progressively more serious stages. In first-degree heart block, although all impulses are conducted through the AV junction, conduction time to the ventricles is abnormally prolonged. In second-degree heart block, some impulses are conducted to the ventricles, whereas some are not. In third-degree heart block, no impulses from the natural pacemaker are conducted to the ventricles. This results in a slower ventricular contraction rate. The rate of contraction in this case is usually determined by the rate of the fastest depolarizing His-Purkinje cell distal from the block site. Typically, heart rates in third-degree block are in the 20 to 60 bpm range, but can also be as low as zero in some cases.

Arrhythmias resulting from cardiac conduction disturbances can be treated with a variety of drugs that inhibit specific aspects of the cardiac action potentials and inhibit the production or conduction of impulses along abnormal pathways. Drugs used to treat these arrhythmias block the fast $Na^+$ channels (quinidine, procainamide, lidocaine), block the slow $Ca^{++}$ channel (verapamil), or block β-adrenergic receptors (propranolol).

The cardiac conduction system, or electrical activation of the heart, involves the transfer of current, in the form of chemical ion gradients, from one myocardial cell to another. Conductive proteins in cardiac cells facilitate this transfer of current. Individual cardiac cells express a plurality of gap junction channel proteins, through which ions traverse. The intercellular channels of gap junctions are assembled from individual membrane-spanning connexin proteins, several of which have been cloned and sequenced in mammals. These proteins facilitate the transfer of ions from cell to cell and are responsible for electronic coupling of cells. Saffitz, et al., *J. Card. Electrophys.*, 1995, 6, 498–510.

Connexin proteins comprise a family of related proteins and include, for example, Cx43 (Fishman, et al., *J. Cell Biol.*, 1990, 111, 589–598), and Cx40 and Cx45 (Kanter, et al., *J. Mol. Cell Cardiol.*, 1994, 26, 861–868). Cx43 appears to be the most abundant connexin in the heart, with expression in the ventricle and atrial myocardium, and distal bundle of His and Purkinje fibers, while being absent from the SA node, AV node, and proximal bundle of His. Gourdie, et al., *J. Cell Sci.*, 1993, 105, 985–991, and Davis, et al., *J. Am. Coll. Cardiol.*, 1994, 24, 1124–1132. Cx40 is most abundantly expressed in the atrial myocardium, and in the distal bundle of His and Purkinje fibers, while present at reduced levels in the ventricular myocardium, and the nodes. Gourdie, et al., *J. Cell Sci.*, 1993, 105, 985–991, and Davis, et al., *J. Am. Coll. Cardiol.*, 1994, 24, 1124–1132. Cx45 is moderately expressed in the ventricle and atrial myocardium, and distal bundle of His and Purkinje fibers, while present at lower levels in the SA node, AV node, and proximal bundle of His. Gourdie, et al., *J. Cell Sci.*, 1993, 105, 985–991, and Davis, et al., *J. Am. Coll. Cardiol.*, 1994, 24, 1124–1132. Cx43 and Cx40 connexins are relatively fast conductive proteins, whereas Cx45 is a relatively slow conductive protein.

Gene therapy has recently emerged as a powerful approach to treating a variety of mammalian diseases. Direct transfer of genetic material into myocardial tissue in vivo has recently been demonstrated to be an effective method of expressing a desired protein. For example, direct myocardial transfection of plasmid DNA by direct injection into the heart of rabbits and pigs (Gal, et al., *Lab. Invest.*, 1993, 68, 18–25), as well as of rats (Ascadi, et al., *The New Biol.*, 1991, 3, 71–81), has been shown to result in expression of particular reporter gene products. In addition, direct in vivo gene transfer into myocardial cells has also been accomplished by directly injecting adenoviral vectors into the myocardium. French, et al., *Circulation*, 1994, 90, 2415–2424, and PCT Publication WO 94/11506.

It has long been desired to effectively treat conduction pathway abnormalities. To this end, conventional procedures including drug therapy, pacemaker technology, or a combination thereof, have been employed. In contrast to these therapeutic procedures, Applicants' invention is directed to treating and/or correcting disturbances in the cardiac conduction pathway by using delivery systems to deliver conduction protein genetic material into myocardial tissue. In patients with cardiac conduction disturbances, it is desirable to locate the problematic area within the heart, and either treat the problematic cells to restore proper cardiac conduction or enhance the cardiac conduction of normal cells surrounding the problematic area. For example, in a patient with heart block, a tract of normal, healthy cells surrounding the scar in the ventricle, which is causing the heart block, is identified and treated by expressing cardiac conduction proteins, such as, for example, gap junction proteins to impart a faster or otherwise enhanced conduction system. In this case, the block can be effectively bridged, or shunted, resulting in a QRS of a width intermediate between a normally conducted beat and a PVC.

SUMMARY OF THE INVENTION

In accordance with the above, the primary purpose of Applicants' claimed invention is to provide methods and delivery systems for treating cardiac conduction disturbances. Upon identifying a problematic area within the heart, conduction protein genetic material is selected such that expression of a selected conduction protein corrects or improves the cardiac conduction of the cells in the problematic area. Alternatively, expression of a selected conduction protein can improve the cardiac conduction of normal, healthy cells surrounding the problematic cells. Improvement of cardiac conduction can be manifested by a replacement, a speeding up, or a slowing down of the existing conduction pathway. The conduction protein genetic material comprises recombinant nucleic acid molecules comprising a nucleic acid molecule encoding the conduction protein inserted into a delivery vehicle, such as, for example, plasmids or adenoviral vectors, and the appropriate regulatory elements. Alternatively, the conduction protein genetic material comprises the conduction protein itself Expression of the desired conduction protein from recombinant nucleic acid molecules is controlled by promoters, preferably cardiac tissue-specific promoter-enhancers, operably linked to the nucleic acid molecule encoding the conduction protein. The conduction protein is preferably a gap junction protein, such as, for example, the connexins Cx40, Cx43, and Cx45, which is used to correct or improve the cardiac conduction of cells within the problematic area. For example, if the cardiac conduction pathway disturbance is a heart block or bradycardia, Cx43 or Cx40 is preferably used. However, if the cardiac conduction pathway disturbance is tachycardia, Cx45 is preferably used. The cardiac conduction genetic material is delivered to specific sites within the heart by perfusion or injection of a therapeutically effective amount, which is that amount which corrects or improves the cardiac conduction of the myocardial cells. The therapeutically effective amount can be delivered to the specific site in the heart in a single dose or multiple doses, as desired.

In carrying out the treatment provided by this invention, the nature of the patient's cardiac conduction disturbance is first studied to determine whether the patient presents a condition which is addressable by genetically modifying a selected cardiac conduction pathway in accordance with this invention. Given this condition, the patient's heart is mapped using known mapping techniques, and the disturbance is located. The appropriate conduction protein genetic material is then selected, which step includes selection of the nucleic acid molecule encoding the conduction protein, delivery vehicle, and the appropriate regulatory elements, etc., as noted above. It is also determined what dose is indicated for treating the disturbance, depending upon the particular cardiac conduction disturbance that is diagnosed, and whether follow-up treatments require implantation of an externally controllable delivery system. The determined conduction protein genetic material is prepared, and loaded into the delivery system. The treatment is then effected by utilizing the delivery system to deliver the therapeutic dose to the patient, e.g., either injecting the material or perfusing the selected area of the heart.

The present invention further provides a delivery system for delivering a therapeutically effective amount of a predetermined conduction protein genetic material to an identified cardiac location, the genetic material being selected for altering the conductivity of cardiac cells to which it is delivered. The delivery system includes the selected genetic material contained in a reservoir, and a catheter subsystem for delivering the genetic material from the reservoir to the identified cardiac location so as to contact a plurality of cells in the proximity of the selected cardiac location.

The delivery system may utilize an external reservoir for providing the genetic material, or alternately may utilize an implantable reservoir. In either embodiment, a controllable pump mechanism is provided for transferring therapeutic doses of the genetic material from the reservoir, through a catheter, and to the selected cardiac location. The catheter subsystem may be of a type for direct introduction into the myocardium, as with a transthoracic procedure, or, more preferably, a endocardial catheter having a distal tip portion adapted for positioning and injecting the genetic material into the myocardium from within a heart chamber. In a preferred embodiment, the catheter distal tip has a normally withdrawn helical needle, which is extendable when positioned in the vicinity of the selected site so as to be screwed into the heart. The needle is hollow and connects with the catheter lumen so as to receive the pumped genetic material; it has one or more ports located so as to effectively release the genetic material for transduction into the mapped area. In another preferred embodiment of the invention, the delivery system is combined with the mapping catheter such that once the selected site is identified, the delivery system, which is within the mapping catheter, is engaged without removing the mapping catheter. The delivery system can be used for one treatment and then removed, or can be implanted for subsequent treatments, in which latter case it is controllable by an external programmer type device.

BRIEF DESCRIPTION OF THE DRAWINGS

FIG. 3 is a schematic drawing of the distal portion of a catheter, which can be extendable and retractable, used for injecting a solution carrying chosen genetic material into a patient's heart.

FIG. 4 illustrates the distal end of a catheter, having a distal portion which encloses an osmotic pump.

DESCRIPTION OF THE PREFERRED EMBODIMENTS

Figure 1:
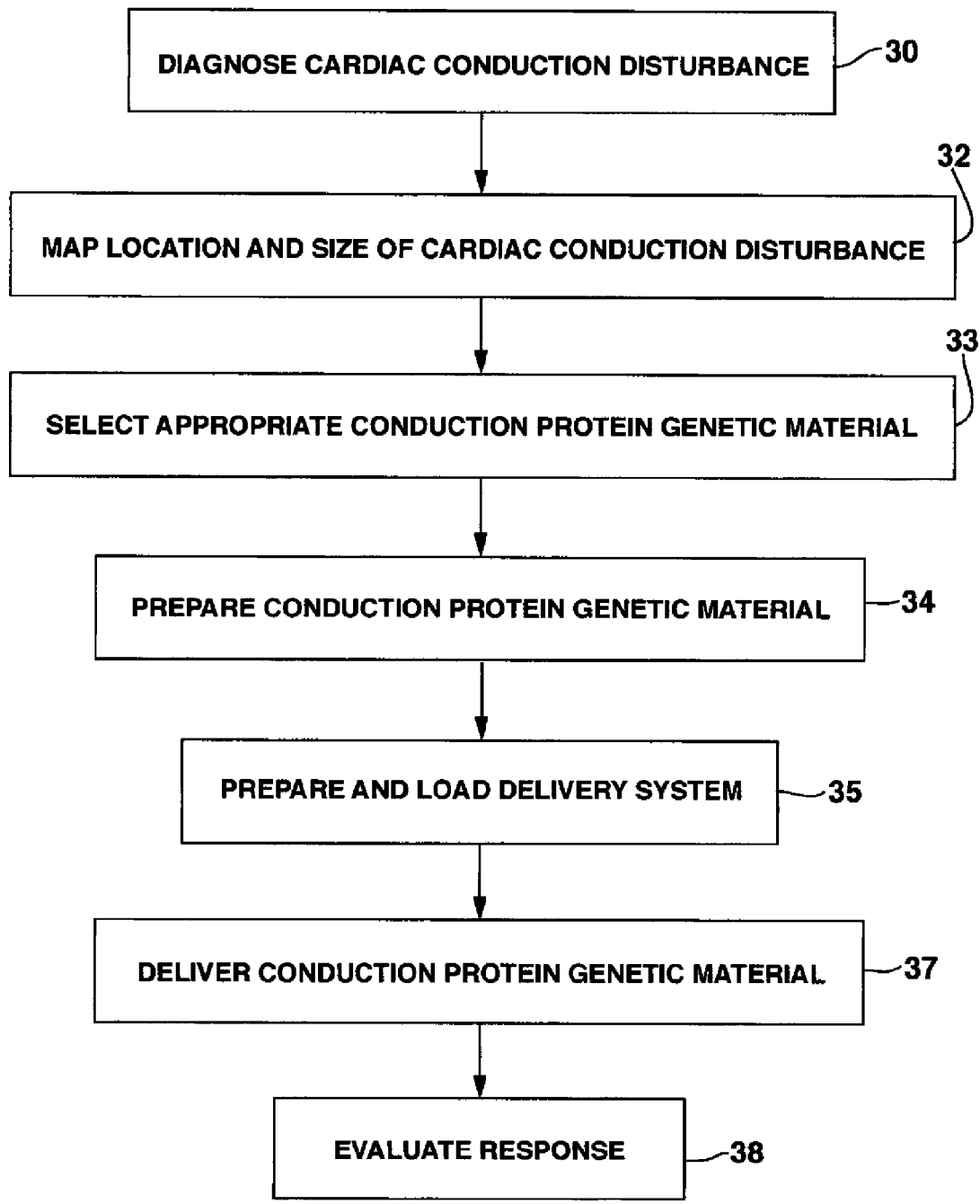
FIG. 1 is a flow diagram presenting the primary steps involved in the practice of this invention, including mapping the patient's conductive system to determine the location of the problem, choosing an appropriate genetic material, and expressing the genetic material in an appropriate dose into the determined location.

Applicants' invention provides methods and delivery systems for treating cardiac conduction pathway disturbances. A problematic area exhibiting, for example, SSS, "brady-tachy syndrome," bradycardia, tachycardia, or heart block, within the heart is identified by routine and conventional techniques known to the skilled artisan. Once the specific problem has been identified, conduction protein genetic material is selected such that expression of a selected conduction protein corrects or improves the cardiac conduction of the problematic cells or improves the cardiac conduction of normal cells surrounding the problematic cells. The conduction protein genetic material comprises either the conduction protein itself or recombinant nucleic acid molecules comprising a nucleic acid molecule encoding the conduction protein inserted into a delivery vehicle, such as, for example, plasmid, cosmid, YAC vector, viral vectors, and the like, and the appropriate regulatory elements. In preferred embodiments of the present invention, the nucleic acid molecule encoding the conduction protein is the full length coding sequence cDNA of a conduction protein, and is inserted into a plasmid or adenoviral vector, such as, for example, pGEM3 or pBR322, and Ad5, respectively. The regulatory elements are capable of directing expression in mammalian cells, specifically human cells. The regulatory elements include a promoter and a polyadenylation signal. Expression of the desired conduction protein is preferably controlled by cardiac tissue-specific promoter-enhancers, operably linked to the nucleic acid molecule encoding the conduction protein. The conduction protein is preferably a gap junction protein, such as, for example, the connexins Cx40, Cx43, and Cx45, which is used to correct or improve the cardiac conduction of cells within the problematic area. The specific gap junction protein chosen is dependent upon the nature of the identified problem. For example, where the conduction is slow or non-existent, such as in heart block or bradycardia, introduction of Cx40 or Cx43 would enhance conduction. In contrast, introduction of the slower conducting Cx45 into the AV node and His tissues would result in the prevention of brady-tachy syndrome and tachycardia. The conduction protein genetic material is preferably delivered in a pharmaceutical composition comprising, for example, the conduction protein genetic material in a volume of phosphate-buffered saline with 5% sucrose. The cardiac conduction genetic material is delivered to specific sites within the heart by perfusion or injection of a therapeutically effective amount, which is that amount which corrects or improves the cardiac conduction of the myocardial cells. The therapeutically effective amount can be delivered to the specific site in the heart in single or multiple doses, as desired, using the delivery systems of the invention.

The present invention also comprises a delivery system for delivering a therapeutically effective amount of conduction protein genetic material to a mapped cardiac location in such a way as to enhance the effective conduction of the myocardial cells around the area of disturbance. In a first embodiment, the delivery system basically comprises a reservoir subsystem for holding the genetic material, and a catheter subsystem in communication with the reservoir subsystem for placement of the genetic material in and around the identified cardiac location. As seen in the following discussion of several preferred embodiments, the reservoir subsystem and catheter subsystem may be separate, or they may be combined. Preferably the reservoir contains up to 25 ml of a genetic material for delivery to the myocardium. In some applications, only a bolus of about 0.1–10 ml, or more preferably 1–5 ml, is delivered to the targeted areas. In other applications, such as where conduction protein is being delivered in repeated doses, 25 ml or more may be used. Also, the genetic material may be diluted in a saline solution, such as, for example, phosphate-buffered saline (PBS), the reservoir holding the diluted solution for controlled delivery. Additionally, it is to be understood that the reservoir and associated control apparatus may be either implantable or external to the body, depending upon the circumstances, e.g., whether metered doses are to be administered to the patient over a period of time, or whether the delivery of the genetic material is essentially a one time treatment.

Referring now to FIG. 1, the primary steps involved in the practice of this invention are shown in the flow diagram. As illustrated in 30, the first step is to determine the nature of the cardiac conduction disturbance, which can manifest itself in ineffective or harmful conductive properties. This step can constitute diagnosis of SSS, "brady-tachy syndrome," bradycardia, tachycardia, heart block, etc. The next step, illustrated in 32, is mapping the patient's heart to determine the location, size and extent of the disturbance of problematic area. Intracardiac electrocardiographic techniques, or electrophysiology (EP) studies, permit a detailed analysis of the mechanisms of cardiac impulse formation and conduction. The testing and mapping protocol utilized and the sites selected for recording depend upon the symptoms manifested in the individual. One skilled in the art is readily familiar with cardiac mapping techniques, such as, for example, those described in U.S. Pat. No. 4,699,147, U.S. Pat. No. 5,297,549, and U.S. Pat. No. 5,397,339, all of which are incorporated by reference. The mapping techniques known to those skilled in the art will readily identify those cardiac locations encompassing cardiac cells with abnormal conduction properties. As shown in 33, the next step is to select the appropriate conduction protein genetic material. This selection, which yields the "preselected genetic material," is dependent upon the nature of the cardiac conduction disturbance, as discussed below. The conduction protein genetic material is next prepared, as illustrated in 34, by either inserting the nucleic acid molecules encoding the appropriate conduction protein into a delivery vehicle with the appropriate regulatory elements, in the case of a recombinant nucleic acid molecule, or expressing the conduction protein from an expression vector, in the case of the conduction protein itself. As shown in 35, the next step is to prepare and load the delivery system with a therapeutically effective amount of the conduction protein genetic material. As illustrated in 37, the next step comprises administering the therapeutically effective amount to the patient by contacting the appropriate location in the heart, as determined earlier, using the delivery system described herein. An alternative method of administering the therapeutically effective amount of the conduction protein genetic material is to directly inject the heart of the patient. The final step, shown in 38, is to evaluate the response of the patient to the treatment.

Figure 2:
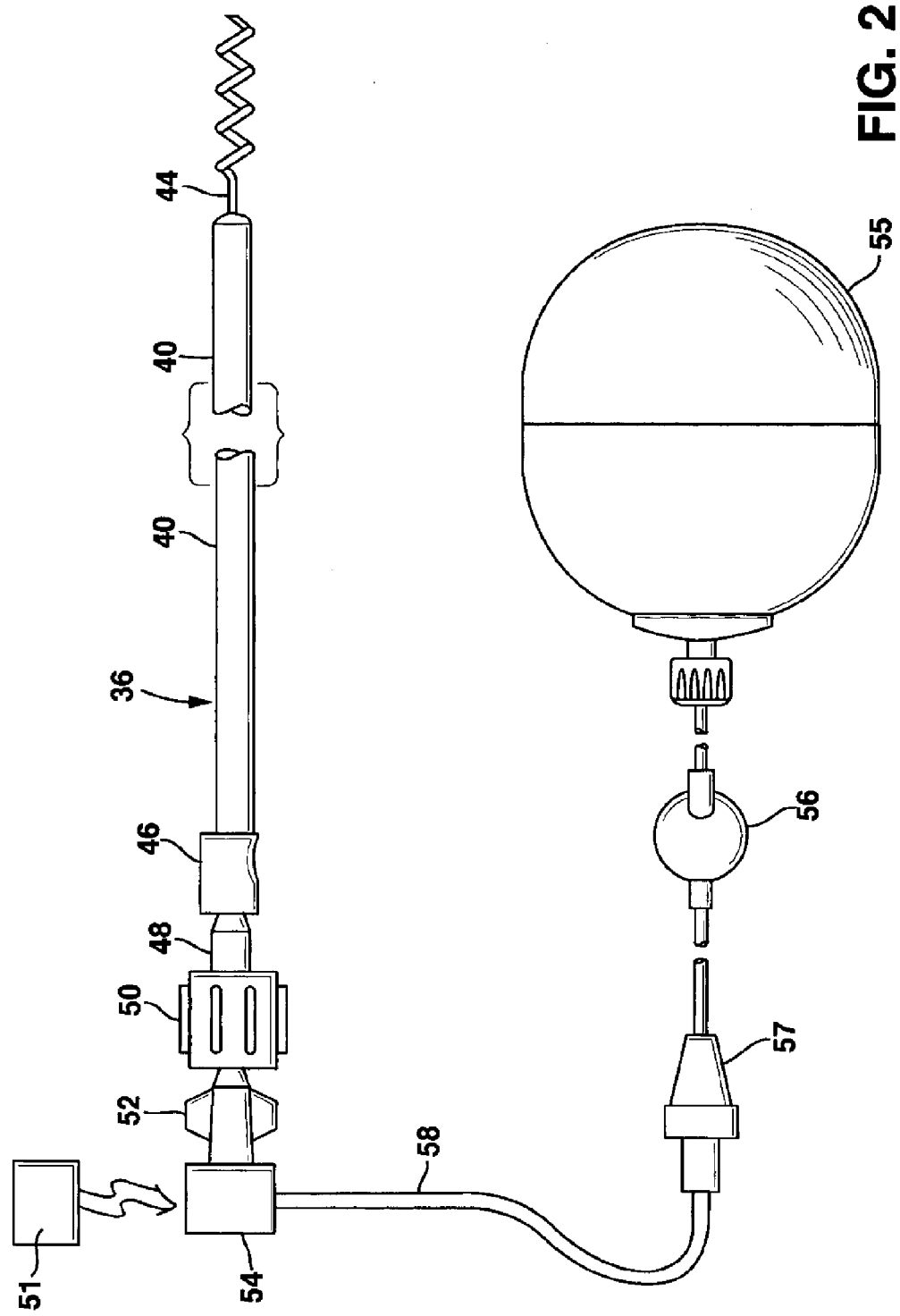
FIG. 2 is a schematic representation of a delivery system in accordance with this invention, illustrating delivery of genetic material into a patient's heart at the chosen location.

Referring now to FIG. 2, there is shown an illustrative embodiment of a delivery system useful for certain applications of this invention, e.g., where larger amounts of genetic material alone or in solution are employed. A catheter 36, preferably a transvenous catheter, includes an elongated catheter body 40, suitably an insulative outer sheath which may be made of polyurethane, Teflon, silicone, or any other acceptable biocompatible plastic. The catheter has a standard lumen (illustrated in FIG. 3) extending therethrough for the length thereof, which communicates through to a hollow helical needle element 44, which is adapted for screwing into the patient's myocardium. The outer distal end of helical element 44 is open, permitting genetic material in fluid form to be dispensed out of the end, as is discussed in more detail below in connection with FIG. 3. At the proximal end of the catheter, a fitting 46 is located, to which a Luer lock 48 is coupled. Luer lock 48 is coupled to the proximal end of elongated catheter body 40 and receives the lumen. A swivel mount 50 is mounted to Luer lock 48, allowing rotation of the catheter relative to Luer lock 52. Luer lock 52 in turn is coupled through control element 54 to a tube 58 which communicates with reservoir 55, suitably through flow control 57 and filter 56. Reservoir 55 holds a supply of the selected genetic material. Control elements 57 and 54 are used for adjustment of the pressure and flow rate, and may be mechanically or electronically controlled. Thus, unit 54 or 57 may be used to control either rate of delivery, or dosage size, or both. Control unit 54 may be programmed to automatically release predetermined doses on a timed basis. Further, for an implanted system, control unit 54 may be activated from an external programmer as illustrated at 51. Reference is made to international application published under the PCT, International Publication No. WO 95/05781, incorporated herein by reference, for a more detailed description of such a reservoir and catheter combination. It is to be understood that such a system is useful for this invention only for applications where larger fluid amounts are to be expressed, e.g., where a diluted saline solution is used to wash or perfuse a selected area.

Referring now to FIG. 3, there is shown in expanded detail a schematic of the distal end of the catheter of FIG. 2, illustrating the interconnection of the helical element 44 with the interior of the catheter. As illustrated, the helical needle 44 is provided with an internal lumen 59 which is in communication with the internal lumen 63L of the lead formed by tube 63. In this embodiment, helical element 44 may also be a pacing electrode, in which case it is formed of conductive material and welded, crimped, swaged, or connected by other means so as not to prevent fluid flow to tip element 61. Tip element 61 in turn is electrically connected to a conductor coil or coils 64, 65, which extend the length of the lead and are connected to a pacemaker. An outer membrane 60 forms the outer wall of elongated catheter body 40, shown in FIG. 2. Further referring to FIG. 3, element 44 has an outlet 75 where the genetic material may be expressed, and holes or ports 76, 77, and 78 may also be utilized for providing exits for the genetic material which is supplied through lumen 59 under a pressure of up to about one atmosphere from reservoir 55 and the control elements.

In practice, a catheter 36 of the form illustrated in FIGS. 2 and 3 is advanced to the desired site for treatment, which site or location has been previously identified by means of cardiac mapping, as discussed above. The catheter may be guided to the indicated location by being passed down a steerable or guidable catheter having an accommodating lumen, for example as disclosed in U.S. Pat. No. 5,030,204; or by means of a fixed configuration guide catheter such as illustrated in U.S. Pat. No. 5,104,393. Alternately, the catheter may be advanced to the desired location within the heart by means of a deflectable stylet, as disclosed in PCT Patent Application WO 93/04724, published Mar. 18, 1993, or by a deflectable guide wire as disclosed in U.S. Pat. No. 5,060,660. In yet another embodiment, the helical element 44 may be ordinarily retracted within a sheath at the time of guiding the catheter into the patient's heart, and extended for screwing into the heart by use of a stylet. Such extensible helical arrangements are commercially available and well known in the pacing art.

It is to be understood that other forms of the reservoir subsystems and catheter subsystems are within the scope of this invention. Reservoir embodiments include, for example, drug dispensing irrigatable electrodes, such as those described in U.S. Pat. No. 4,360,031; electrically controllable, non-occluding, body implanting drug delivery system, such as those described in U.S. Pat. No. 5,041,107; implantable drug infusion reservoir such as those described in U.S. Pat. No. 5,176,641; medication delivery devices such as those described in U.S. Pat. No. 5,443,450; and infusion pumps, such as SYNCHROMED made by Medtronic, Inc.; and osmotic pumps such as those made by Alza.

Referring now to FIG. 4, there is shown, by way of illustration, another embodiment of a delivery system having a combined catheter and reservoir, useful for applications involving delivery of a relatively small bolus of genetic material, e.g., 1–5 ml. FIG. 4 illustrates the distal end of a catheter, having a distal portion 70 which encloses an osmotic pump. See U.S. Pat. No. 4,711,251, assigned to Medtronic, Inc., incorporated herein by reference. The pump includes an inner chamber 68 and an outer chamber 66, which chambers are separated by an impermeable membrane 67. A semi-permeable outer membrane 72 forms the outer wall of chamber 66. The tubular portion 74 of the helical member connects to lumen 74L within inner chamber 68. A conductor 80, which runs the length of the catheter, extends into the inner chamber 68 and connects with extension 74E as shown at 74C to provide electrical contact through to element 44, in an application which the element 44 is used as a pacing electrode. A seal 79 is provided at the point where the conductor passes through outer membrane 72 and inner membrane 67. An insulating cover 86 encompasses the conductor 80 from the point of contact with seal 79. An end cap 73, which may be integral with outer membrane 72 closes the chamber. Alternately, end cap 73 may be constructed to elute a predetermined medication, such as, for example, steroids. Steroids, such as dexamethasone sodium phosphate, beclamethasone, and the like, are used to control inflammatory processes.

In this arrangement, prior to inserting the catheter distal end into the patient's heart, the inner chamber 68 is charged with the genetic material which is to be dispensed into the myocardium. This may be done, for example, by simply inserting a micro needle through end cap 73, and inserting the desired bolus of genetic material into chamber 68. After the chamber 68 is filled and the catheter is implanted, body fluids will enter chamber 66 through membrane 72 to impart a pressure on the inner chamber 68 via the impermeable membrane 67. This results in a dispensing of the genetic material stored within chamber 68 through the lumen 74L of extension 74E and the helical element 44. Although the preferred needle or element 44 is helical, additional configurations of needles or elements can also be used as known to those skilled in the art.

Still referring now to FIG. 4, there is illustrated another embodiment of a catheter tip useful for delivering a small bolus of the selected genetic material. In this embodiment, the bolus of material is stored within the hollow interior of helical element 44, i.e., the interior is the reservoir. The interior reservoir is maintained sealed by use of a soluble material which is normally solid, but which dissolves when subjected to body fluids for a period of time. An example of such material is mannitol, which can be used when the delivery system is not preloaded with the conduction protein genetic material. Plugs or globules 81–85 of mannitol are illustrated (by dashed lines) in place to block the two ends of element 44, as well as the ports 76, 77, 78. In instances where the conduction protein genetic material is preloaded into the delivery system, a shape memory metal can be used in place of the mannitol. Such metals are well known to the skilled artisan. Either of these features can be combined with an osmotic pump, as described in connection with FIG. 3, where the outer chamber is filled with a saline solution which forces the genetic material out of the ports of element 44. Alternatively, the outer chamber can be filled with the genetic material, which is then forced out of the ports of element 44. Another alternate embodiment, not shown, is to use a stylet which inserted through to the distal end of the catheter, to push a piston which aids in expressing the genetic material into the myocardial cells.

Figure 5:
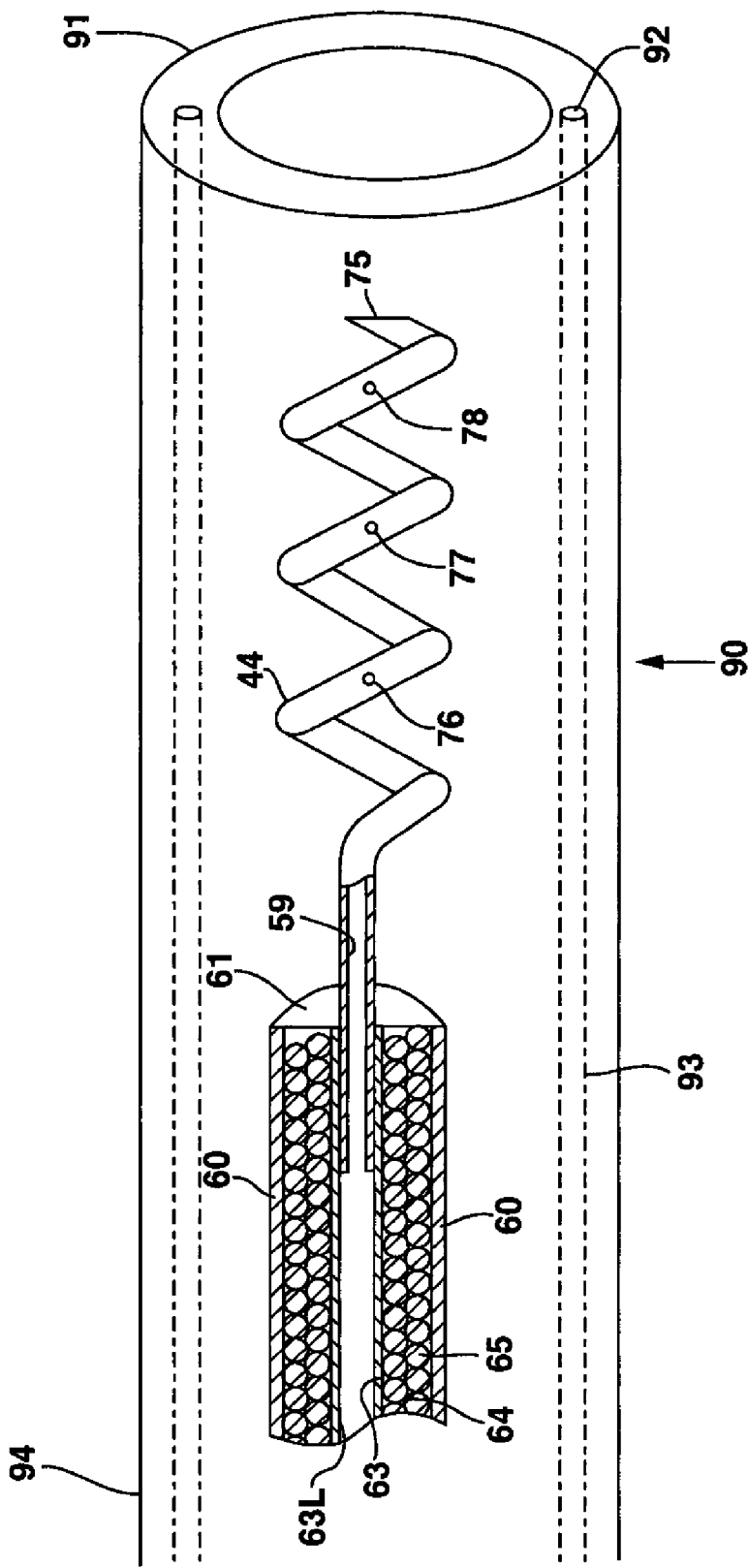
FIG. 5 illustrates a delivery system in which the delivery means comprises a mapping catheter combined with a delivery system for injecting a solution carrying chosen genetic material into a patient's heart.

Although a transvenous form of delivery system is preferred, it is to be understood that the invention can employ other methods and devices. For example, a small bolus of selected genetic material can be loaded into a micro-syringe, e.g., a 100 1 Hamilton syringe, and applied directly from the outside of the heart. Referring now to FIG. 5, there is shown, by way of illustration, another embodiment of a delivery system having a combined mapping catheter and delivery means. The delivery system of this embodiment comprises a catheter 90 with a distal end 91 having an opening at the distal end. The catheter 90 further comprises mapping electrode means 92 at the distal end 91. The mapping electrode means carries out the mapping of the patient's heart. Conductor means 93 electrically connects the mapping electrode means 92 to the proximal end 94 of the catheter 90. The delivery system further comprises a delivery means within the catheter. The embodiment of the delivery means illustrated in FIG. 5 is the delivery means shown in FIG. 3. However, any of the delivery means described herein can be used in combination with the mapping catheter shown in FIG. 5. The catheter 90 is inserted into the patient's heart and the site located by routine mapping procedures. Once a site is identified in the heart, the mapping catheter 90 remains in place and the delivery means is then extended through the distal end 91 of the catheter 90, and the heart tissue or cells is contacted with the conduction protein genetic material. In another embodiment of the invention, the catheter 90 is a peelable introducer sheath, with two conductor means 93 electrically connecting the introducer sheath, which serves to map the heart, to electrode means 92. Once the cardiac site is mapped, the delivery means is contacted with the heart tissue, and the introducer is removed and peeled away.

Figure 6A:
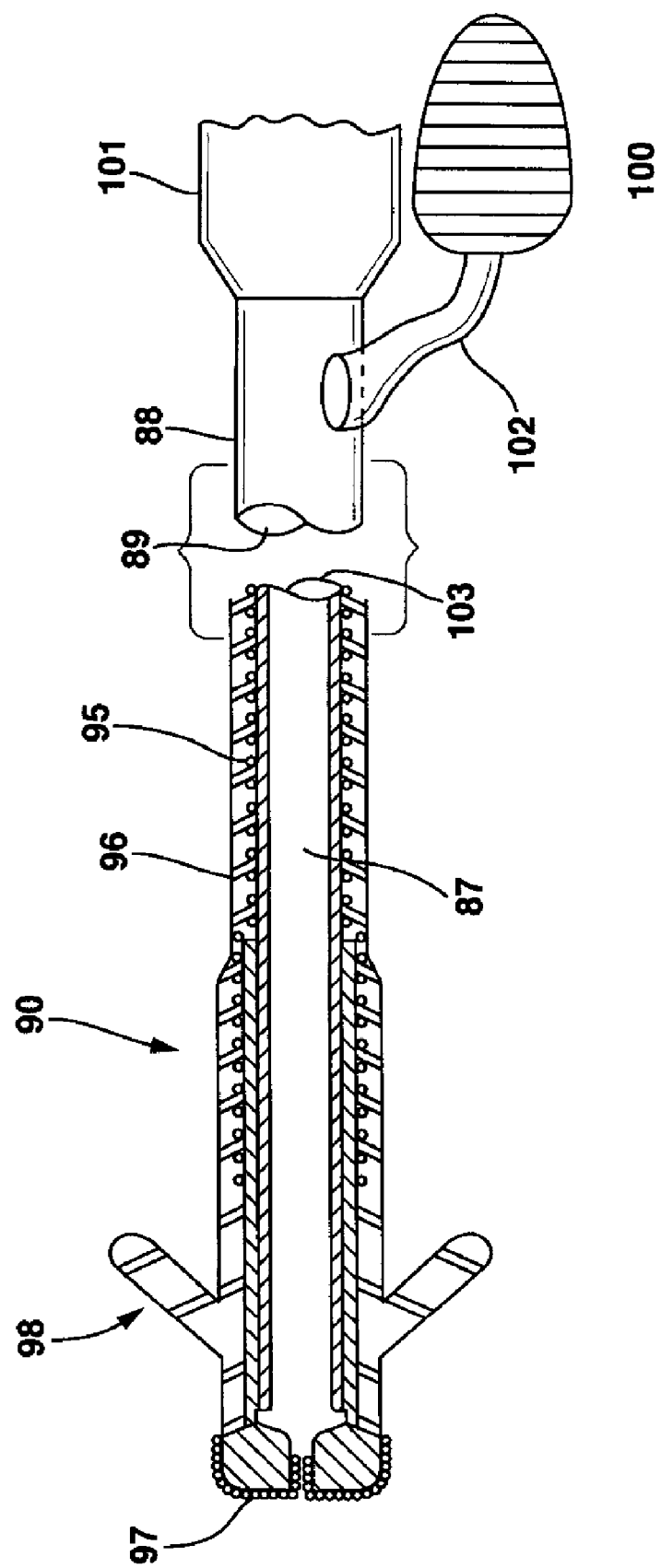
FIG. 6A is a schematic representation of a delivery system in accordance with this invention, having a combined catheter and pacing lead, with a separate pump.

Referring now to FIG. 6A, there is shown, by way of illustration, another embodiment of an implantable delivery system comprising a combined pacing lead and delivery catheter, hereinafter referred to simply as a catheter. In this embodiment, the catheter 90 is combined with a pacemaker or pulse generator (not shown) and a source of genetic material such as illustrated by pump 100 which is suitably implanted near the pacemaker. The proximal end 101 of the catheter is connected to the pacemaker in the standard fashion. The genetic material is delivered through connecting tube 102 to a proximal section 88 of the catheter, communicating with lengthwise catheter lumen illustrated at 89. Alternately, the pacemaker head may contain a reservoir and micropump, for providing delivery of the genetic material directly to the lumen 89. The main length of the catheter has an outside sheath of biocompatible insulating material 96, and at least one conductor coil 95 which communicates electrically from the pacemaker to electrode 97 at the distal tip of the catheter. The catheter further comprises an axially positioned polymeric cannula 103, having lumen 87, through at least a portion of the catheter length and positioned within coil 95, which provides an inner surface for the catheter lumen. The cannula terminates at the distal end of the catheter, just proximal to the tip portion of electrode 97, which is illustrated as having an outer porous surface. Electrode 97 has a central opening, shown covered with the porous electrode material, through which genetic material can pass when the catheter is positioned in the patient. As shown, conductor coil 95 is electrically connected to electrode 97, and connects pace pulses and sensed cardiac signals between the pacemaker and the electrode. Of course, for a bipolar embodiment, the lead/catheter 90 carries a second electrode (not shown), suitably a ring electrode just proximal to electrode 97. Also, as illustrated, a fixation mechanism such as tines 98 are employed for fixing or anchoring the distal tip to the heart wall of the patient.

In one embodiment, pump 100 is suitably an osmotic minipump, which pumps fluid contained within through tube 102, into catheter portion 88 and through lumens 89, 87 to the tip electrode 97. As mentioned previously, the reservoir and pump may alternately be mounted in the pacemaker device itself. In either instance, the genetic material is delivered under very minimal pressure from the reservoir through the lumen of the catheter to the electrode, where it is passed through the electrode central channel to contact myocardial cells. In yet another embodiment, the lumen portion 87 provided by the cannula is utilized as the reservoir. In this embodiment, delivery may either be passive, or with the aid of a micropump (not shown). The genetic material can be preloaded into the cannula, or it can be inserted by a needle just before the catheter is introduced and positioned with the patient.

Figure 6B:
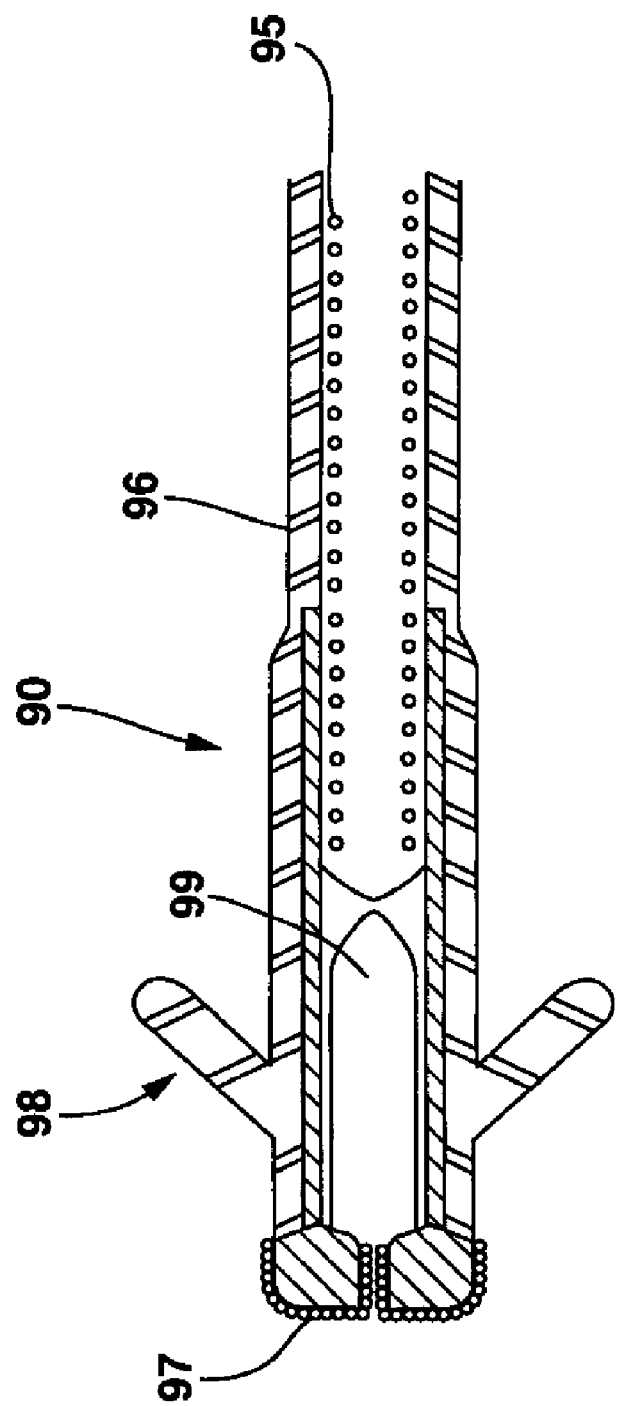
FIG. 6B is another embodiment of a combined pacing lead and delivery catheter having a reservoir located at the distal end of the catheter.

In another embodiment, as illustrated in FIG. 6B, a chamber 99 is provided just proximal from eluting electrode 97, and serves as the reservoir of the genetic material. Insulating material 96 is formed from a self-sealing material such that it may be pierced with a needle, or the like, and reseal itself, thus allowing introduction of the genetic material into the chamber prior to implantation. Alternately, insulating material 96 can contain a port (not shown) through which the needle inserts the genetic material. In this embodiment, delivery of the material is without a pump, i.e., passive, the material draining slowly through the microporous portion of electrode 97.

As used herein, the phrase "cardiac conduction disturbance" refers to disturbances or disruptions of the normal cardiac conduction system in a mammal. Such disturbances may be the result of congenital phenomena or trauma, and can manifest in conditions such as, for example, sick sinus syndrome, "brady-tachy syndrome," heart block, bradycardia, tachycardia, and other arrhythmatic conditions. Manifestations of such cardiac conduction disturbances have been traditionally treated by drugs, artificial conduction systems such as pacemakers, ablation therapy, or a combination thereof.

As used herein, the phrase "conduction protein genetic material" refers to recombinant nucleic acid molecules encoding the conduction proteins or, alternatively, the conduction proteins themselves, which are used in the methods and delivery systems of the invention. For chronic treatment, or long term treatment, the conduction protein genetic material will be in the form of recombinant nucleic acid molecules encoding the conduction protein. In contrast, for acute treatment, or short term treatment, the conduction protein genetic material will be in the form of the conduction proteins themselves. Once the conduction protein genetic material has been selected, it is referred to as "predetermined genetic material."

A "recombinant nucleic acid molecule", as used herein, is comprised of an isolated conduction protein-encoding nucleotide sequence inserted into a delivery vehicle. Regulatory elements, such as the promoter and polyadenylation signal, are operably linked to the nucleotide sequence encoding the conduction protein, whereby the protein is capable of being produced when the recombinant nucleic acid molecule is introduced into a cell.

The nucleic acid molecules encoding the conduction proteins are prepared synthetically or, preferably, from isolated nucleic acid molecules, as described below. A nucleic acid is "isolated" when purified away from other cellular constituents, such as, for example, other cellular nucleic acids or proteins, by standard techniques known to those of ordinary skill in the art. The coding region of the nucleic acid molecule encoding the conduction protein can encode a full length gene product or a subfragment thereof, or a novel mutated or fusion sequence. The protein coding sequence can be a sequence endogenous to the target cell, or exogenous to the target cell. The promoter, with which the coding sequence is operably associated, may or may not be one that normally is associated with the coding sequence.

The nucleic acid molecule encoding the conduction protein is inserted into an appropriate delivery vehicle, such as, for example, an expression plasmid, cosmid, YAC vector, and the like. Almost any delivery vehicle can be used for introducing nucleic acids into the cardiovascular system, including, for example, recombinant vectors, such as one based on adenovirus serotype 5, Ad5, as set forth in French, et al., Circulation, 1994, 90, 2414–2424, which is incorporated herein by reference. An additional protocol for adenovirus-mediated gene transfer to cardiac cells is set forth in WO 94/11506 and in Barr, et al., Gene Ther., 1994, 1, 51–58, both of which are incorporated herein by reference. Other recombinant vectors include, for example, plasmid DNA vectors, such as one derived from pGEM3 or pBR322, as set forth in Acsadi, et al., The New Biol., 1991, 3, 71–81, and Gal, et al., Lab. Invest., 1993, 68, 18–25, both of which are incorporated herein by reference, cDNA-containing liposomes, artificial viruses, nanoparticles, and the like. It is also contemplated that conduction proteins be injected directly into the myocardium.

The regulatory elements of the recombinant nucleic acid molecules of the invention are capable of directing expression in mammalian cells, specifically human cells. The regulatory elements include a promoter and a polyadenylation signal. In addition, other elements, such as a Kozak region, may also be included in the recombinant nucleic acid molecule. Examples of polyadenylation signals useful to practice the present invention include, but are not limited to, SV40 polyadenylation signals and LTR polyadenylation signals. In particular, the SV40 polyadenylation signal which is in pCEP4 plasmid (Invitrogen, San Diego, Calif.), referred to as the SV40 polyadenylation signal, can be used.

The promoters useful in constructing the recombinant nucleic acid molecules of the invention may be constitutive or inducible. A constitutive promoter is expressed under all conditions of cell growth. Exemplary constitutive promoters include the promoters for the following genes: hypoxanthine phosphoribosyl transferase (HPRT), adenosine deaminase, pyruvate kinase, -actin, human myosin, human hemoglobin, human muscle creatine, and others. In addition, many viral promoters function constitutively in eukaryotic cells, and include, but are not limited to, the early and late promoters of SV40, the Mouse Mammary Tumor Virus (MMTV) promoter, the long terminal repeats (LTRs) of Maloney leukemia virus, Human Immunodeficiency Virus (HIV), Cytomegalovirus (CMV) immediate early promoter, Epstein Barr Virus (EBV), Rous Sarcoma Virus (RSV), and other retroviruses, and the thymidine kinase promoter of herpes simplex virus. Other promoters are known to those of ordinary skill in the art.

Inducible promoters are expressed in the presence of an inducing agent. For example, the metallothionein promoter is induced to promote (increase) transcription in the presence of certain metal ions. Other inducible promoters are known to those of ordinary skill in the art.

Promoters and polyadenylation signals used must be functional within the cells of the mammal. In order to maximize protein production, regulatory sequences may be selected which are well suited for gene expression in the cardiac cells into which the recombinant nucleic acid molecule is administered. For example, the promoter is preferably a cardiac tissue-specific promoter-enhancer, such as, for example, cardiac isoform troponin C (cTNC) promoter. Parmacek, et al., J. Biol. Chem., 1990, 265, 15970–15976, and Parmacek, et al., Mol. Cell Biol., 1992, 12, 1967–1976. In addition, codons may be selected which are most efficiently transcribed in the cell. One having ordinary skill in the art can produce recombinant nucleic acid molecules which are functional in the cardiac cells.

Genetic material can be introduced into a cell or "contacted" by a cell by, for example, transfection or transduction procedures. Transfection refers to the acquisition by a cell of new genetic material by incorporation of added nucleic acid molecules. Transfection can occur by physical or chemical methods. Many transfection techniques are known to those of ordinary skill in the art including: calcium phosphate DNA co-precipitation; DEAE-dextran DNA transfection; electroporation; naked plasmid adsorption, and cationic liposome-mediated transfection. Transduction refers to the process of transferring nucleic acid into a cell using a DNA or RNA virus. Suitable viral vectors for use as transducing agents include, but are not limited to, retroviral vectors, adeno associated viral vectors, vaccinia viruses, and Semliki Forest virus vectors.

Treatment of cells, or contacting cells, with recombinant nucleic acid molecules can take place in vivo or ex vivo. For ex vivo treatment, cells are isolated from an animal (preferably a human), transformed (i.e., transduced or transfected in vitro) with a delivery vehicle containing a nucleic acid molecule encoding a conduction protein, and then administered to a recipient. Procedures for removing cells from mammals are well known to those of ordinary skill in the art. In addition to cells, tissue or the whole or parts of organs may be removed, treated ex vivo and then returned to the patient. Thus, cells, tissue or organs may be cultured, bathed, perfused and the like under conditions for introducing the recombinant nucleic acid molecules of the invention into the desired cells.

For in vivo treatment, cells of an animal, preferably a mammal and most preferably a human, are transformed in vivo with a recombinant nucleic acid molecule of the invention. The in vivo treatment may involve systemic intravenous treatment with a recombinant nucleic acid molecule, local internal treatment with a recombinant nucleic acid molecule, such as by localized perfusion or topical treatment, and the like. When performing in vivo administration of the recombinant nucleic acid molecule, the preferred delivery vehicles are based on noncytopathic eukaryotic viruses in which nonessential or complementable genes have been replaced with the nucleic acid sequence of interest. Such noncytopathic viruses include retroviruses, the life cycle of which involves reverse transcription of genomic viral RNA into DNA with subsequent proviral integration into host cellular DNA. Retroviruses have recently been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M. "Gene Transfer and Expression, a Laboratory Manual", W.H. Freeman Co., New York (1990) and Murry, E. J. e.d. "Methods in Molecular Biology", Vol. 7, Humana Press, Inc., Cliffton, N.J. (1991).

A preferred virus for contacting cells in certain applications, such as in in vivo applications, is the adeno-associated virus, a double-stranded DNA virus. The adeno-associated virus can be engineered to be replication deficient and is capable of infecting a wide range of cell types and species. It further has advantages such as heat and lipid solvent stability, high transduction frequencies in cells of diverse lineages, including hemopoietic cells, and lack of superinfection inhibition thus allowing multiple series of transductions. Recent reports indicate that the adeno-associated virus can also function in an extrachromosomal fashion.

In preferred embodiments of the present invention, the recombinant nucleic acid molecules comprising nucleic acid molecules encoding the conduction proteins, or, in the alternative, the conduction proteins, are delivered to the cardiac cells of the identified cardiac location, as determined by mapping procedures set forth above, using the delivery systems set forth above. Alternatively, the conduction protein genetic material is delivered to the cardiac cells of the identified cardiac location by direct injection.

In preferred embodiments of the present invention, the nucleic acid molecules encoding the conduction proteins comprise the full length coding sequence cDNA of a conduction protein. Preferably, the conduction proteins are the gap junction proteins; more preferably, they are the connexin proteins. Such nucleic acid molecules are described in the Fishman, et al., J. Cell. Biol., 1990, 111, 589–598, and Kanter, et al., J. Mol. Cell Cardiol., 1994, 26, 861–868 references, both of which are incorporated herein by reference, which contain the full length coding sequence cDNA of the connexin gap junction proteins Cx43, and Cx40 and Cx45, respectively.

Introduction of the gap junction-encoding nucleic acid molecules or the gap junction proteins to normal cardiac cells surrounding a scar causing heart block will result in normal or enhanced conduction. Alternatively, it is proposed that introduction of the gap junction-encoding nucleic acid molecules or the gap junction proteins to abnormal cardiac cells, those cells exhibiting cardiac conduction disturbances, will result in normal or enhanced conduction properties. Determining the appropriate conduction protein genetic material, i.e., determining which connexin protein is appropriate, is dependent upon the particular cardiac conduction disturbance diagnosed. For example, if the cardiac conduction pathway disturbance is a heart block or bradycardia, in which conductance is slowed or non-existent, Cx43 or Cx40, the faster connexins, is preferably used. However, if the cardiac conduction pathway disturbance is tachycardia, in which conductance is too rapid, Cx45 is preferably used.

Nucleic acid molecules comprising nucleotide sequences encoding the connexin proteins Cx40, Cx43, and Cx45 are isolated and purified according to the methods set forth in Fishman, et al, J. Cell. Biol., 1990, 111, 589–598, and Kanter, et al., J. Mol. Cell Cardiol., 1994, 26, 861–868. The nucleic acid and protein sequences of Cx40 are set forth in SEQ ID NO:1 and SEQ ID NO:2, respectively. The nucleic acid and protein sequences of Cx43 are set forth in SEQ ID NO:3 and SEQ ID NO:4, respectively. The nucleic acid and protein sequences of Cx45 are set forth in SEQ ID NO:5 and SEQ ID NO:6, respectively. It is contemplated that nucleic acid molecules comprising nucleotide sequences that are preferably at least 70% homologous, more preferably at least 80% homologous, and most preferably at least 90% homologous to the connexin nucleotide sequences described in SEQ ID NOs 1, 3 and 5, can also be used.

It is understood that minor modifications of nucleotide sequence or the primary amino acid sequence may result in proteins which have substantially equivalent or enhanced activity as compared to the conduction proteins exemplified herein. These modifications may be deliberate, as through site-directed mutagenesis, or may be accidental such as through mutations in hosts which produce the conduction proteins. A "mutation" in a protein alters its primary structure (relative to the commonly occurring or specifically described protein) due to changes in the nucleotide sequence of the DNA which encodes it. These mutations specifically include allelic variants. Mutational changes in the primary structure of a protein can result from deletions, additions, or substitutions. A "deletion" is defined as a polypeptide in which one or more internal amino acid residues are absent as compared to the native sequence. An "addition" is defined as a polypeptide which has one or more additional internal amino acid residues as compared to the wild type protein. A "substitution" results from the replacement of one or more amino acid residues by other residues. A protein "fragment"

is a polypeptide consisting of a primary amino acid sequence which is identical to a portion of the primary sequence of the protein to which the polypeptide is related.

Preferred "substitutions" are those which are conservative, i.e., wherein a residue is replaced by another of the same general type. As is well understood, naturally-occurring amino acids can be subclassified as acidic, basic, neutral and polar, or neutral and nonpolar and/or aromatic. It is generally preferred that encoded peptides differing from the native form contain substituted codons for amino acids which are from the same group as that of the amino acid replaced. Thus, in general, the basic amino acids Lys, Arg, and Histidine are interchangeable; the acidic amino acids Asp and Glu are interchangeable; the neutral polar amino acids Ser, Thr, Cys, Gln, and Asn are interchangeable; the nonpolar aliphatic acids Gly, Ala, Val, Ile, and Leu are conservative with respect to each other (but because of size, Gly and Ala are more closely related and Val, Ile and Leu are more closely related), and the aromatic amino acids Phe, Trp, and Tyr are interchangeable.

While Pro is a nonpolar neutral amino acid, it represents difficulties because of its effects on conformation, and substitutions by or for Pro are not preferred, except when the same or similar conformational results can be obtained. Polar amino acids which represent conservative changes include Ser, Thr, Gln, Asn; and to a lesser extent, Met. In addition, although classified in different categories, Ala, Gly, and Ser seem to be interchangeable, and Cys additionally fits into this group, or may be classified with the polar neutral amino acids. Some substitutions by codons for amino acids from different classes may also be useful.

Once the nucleic acid molecules encoding the connexin proteins are isolated and purified according to the methods described above, recombinant nucleic acid molecules are prepared in which the desired connexin nucleic acid molecule is incorporated into a delivery vehicle by methods known to those skilled in the art, as taught in, for example, Sambrook et al., *Molecular Cloning: A Laboratory Manual*, Second Ed. Cold Spring Harbor Press (1989). Preferred delivery vehicles include, for example, plasmids (Acsadi et al., *The New Biol.*, 1991, 3, 71–81, and Gal, et al., *Lab. Invest.*, 1993, 68, 18–25, both of which are incorporated herein by reference) and adenovirus (WO 94/11506 and in Barr, et al., *Gene Ther.*, 1994, 1, 51–58, both of which are incorporated herein by reference). The nucleic acid molecules encoding connexin proteins, or connexin proteins produced therefrom, are delivered to the cardiac cells of the identified cardiac location by the delivery systems of the present invention. Thus, such delivery systems of the present invention are used to contact the cardiac cells of the identified cardiac location, which comprises cardiac cells having cardiac conduction disturbances, with recombinant nucleic acid molecules encoding a connexin protein, or connexin proteins.

Where the conduction protein genetic material is in the form of conduction proteins, such proteins can be prepared in large quantities by using various standard expression systems known to those skilled in the art. Sambrook et al., *Molecular Cloning: A Laboratory Manual*, Second Ed. Cold Spring Harbor Press (1989), pp. 16.1–16.55, incorporated herein by reference.

The recombinant nucleic acid molecules or connexin proteins are preferably delivered in a pharmaceutical composition. Such pharmaceutical compositions can include, for example, the recombinant nucleic acid molecule or protein in a volume of phosphate-buffered saline with 5% sucrose. In other embodiments of the invention, the recombinant nucleic acid molecule or protein is delivered with suitable pharmaceutical carriers, such as those described in the most recent edition of *Remington's Pharmaceutical Sciences*, A. Osol, a standard reference text in this field. The recombinant nucleic acid molecule or protein is delivered in a therapeutically effective amount. Such amount is determined experimentally and is that amount which either restores normal conduction or improves abnormal conduction of cardiac cells. The amount of recombinant nucleic acid molecule or protein is preferably between 0.01 µg and 100 mg, more preferably between 0.1 µg and 10 mg, more preferably between 1 µg and 1 mg, and most preferably between 10 µg and 1 mg. A single therapeutically effective amount is referred to as a bolus. Where adenovirus vectors are used, the amount of recombinant nucleic acid molecule is preferably between $10^7$ plaque forming units (pfu) and $10^{15}$ pfu, more preferably between $10^8$ pfu and $10^{14}$ pfu, and most preferably between $10^9$ pfu and $10^{12}$ pfu. A single therapeutically effective amount of conduction protein genetic material is referred to as a bolus. In some embodiments of the present invention, the delivery of the recombinant nucleic acid molecules or proteins is combined with steroid elution, such as with dexamethasone sodium phosphate, beclamethasone, and the like, to control inflammatory processes.

The following examples are meant to be exemplary of the preferred embodiments of the invention and are not meant to be limiting.

EXAMPLES

Example 1

Isolation and Purification of Nucleic Acid Molecules Encoding the Connexin Proteins Nucleic acid molecules encoding Cx43, Cx40, and Cx45 are isolated and purified according to general methods well known to those skilled in the art. Briefly, total cellular RNA is isolated and purified (Chomczynsky, et al., *Anal. Biochem.*, 1987, 162, 156–159) from heart tissue, cardiac transplantation donors, or from salvaged tissue, and selected for poly(A) RNA (Sambrook et al., *Molecular Cloning: A Laboratory Manual*, Second Ed. Cold Spring Harbor Press (1989), pp. 7.26–7.29). cDNA corresponding to the connexin proteins is prepared from the poly(A) cardiac RNA by reverse transcription using a GENEAMP™ PCR kit (Perkin Elmer Cetus, Norwalk, Conn.), or the like, using random hexamers according to the manufacturer's instructions. The specific connexin nucleic acid molecules are amplified by the polymerase chain reaction (PCR), also using the GENEAMP™ PCR kit, or the like, using forward and reverse primers specific for each of the different connexin proteins, according to the manufacturer's instructions. For example, the forward primer for Cx43 can be 5'-ATGCCTGACTG-GACCGCCTTAGGC-3' (SEQ ID NO:7), and the reverse primer can be 5'-GATCTCGAGGTCATCAGGCCGAGG-3' (SEQ ID NO:8). For example, the forward primer for Cx45 can be 5'-ATGAGTTGGAGCTTTCTGACTCGC-3' (SEQ ID NO:9), and the reverse primer can be 5'-AATCCAGA-CAGAGTTCTTCCCATC-3' (SEQ ID NO:10). For example, the forward primer for Cx40 can be 5'-ATGGGC-GATTGGAGCTTCCTGGGA-3' (SEQ ID NO:11), and the reverse primer can be 5'-CACTGATAGGTCATCTGACCT-TGC-3' (SEQ ID NO:12). It is understood that additional primers can be used for amplification as determined by those skilled in the art. These primers may be preceded at the 5' terminus by nucleotide sequences containing endonuclease restriction sites for easy incorporation into vectors. The specific connexin nucleic acid molecules can also be amplified by PCR from human genomic DNA (Stratagene, San Diego, Calif.). After cutting the PCR products with the appropriate restriction endonuclease(s), the PCR products are purified by phenol:chloroform extractions, or using commercial purification kits, such as, for example, MAGIC™ Minipreps DNA Purification System (Promega, Madison, Wis.). The specific nucleotide sequence of the PCR products is determined by conventional DNA sequencing procedures, and the identity of the PCR products confirmed by comparison to the published sequences for the connexin proteins.

Example 2

Insertion of Connexin cDNA into Delivery Vehicles

Preferably, connexin cDNA is inserted into either plasmid or adenoviral vectors. Plasmid vectors include for example, pGEM3 or pBR322, as set forth in Acsadi, et al., *The New Biol.*, 1991, 3, 71–81, and Gal, et al., *Lab. Invest.*, 1993, 68, 18–25. Adenoviral vectors include for example, adenovirus serotype 5, Ad5, as set forth in French, et al., *Circulation*, 1994, 90, 2414–2424.

Preferably, the primers used to amplify the connexin nucleic acid molecules are designed with unique endonuclease restriction sites located at the 5' terminus. In the absence of such design, polylinker arms, containing unique restriction sites, can be ligated thereto. After cutting the purified PCR products with the appropriate restriction endonuclease(s), the plasmid vector, comprising a polylinker, is also cut with the same restriction endonuclease(s), affording the connexin nucleic acid molecule a site at which to ligate. In a similar manner, recombinant adenovirus (Gluzman, et al., in *Eukaryotic Viral Vectors*, Gluzman, ed., Cold Spring Harbor Press, 1982, pp. 187–192, and French, et al., *Circulation*, 1994, 90, 2414–2424) containing connexin cDNA molecules are prepared in accordance with standard techniques well known to those skilled in the art.

It is contemplated that variations of the above-described invention may be constructed that are consistent with the spirit of the invention.

---

What is claimed is:

1. An implantable delivery system for delivering doses of genetic material to cardiac tissue, comprising:
    recombinant nucleic acid vectors encoding a conduction protein selected from the group Cx40, Cx43, and Cx45;
    a catheter, said catheter having a distal tip portion for engaging the cells of said cardiac tissue and delivering thereto said recombinant nucleic acid vectors;
    a reservoir means for holding said recombinant nucleic acid vectors, said reservoir means located proximal to the said distal tip portion of said catheter; and
    a delivery means for delivering and transfecting or transducing a therapeutically effective amount of said recombinant nucleic acid vectors from said reservoir means through said distal tip portion of said catheter to said cardiac tissue such that said cardiac tissue is transfected or transduced with said recombinant nucleic acid vectors;
    wherein said catheter additionally comprises a mapping electrode means, a pacing electrode means, and a conductor means for connecting said mapping electrode means and a pacing electrode means to the proximal end of said catheter; and
    wherein said mapping electrode means provides the means of determining the location of said cardiac tissue deficient in connexin expression for transfection or transducing said cells in said cardiac tissue and wherein said pacing electrode means provides means for testing or controlling the effect of the expression of said recombinant nucleic acid vectors with a pacemaker.

* * * * *